United States Patent [19]
Watanabe et al.

[11] Patent Number: 6,135,947
[45] Date of Patent: Oct. 24, 2000

[54] ENDOSCOPE APPARATUS HAVING LIGHT SOURCE MOVABLE BETWEEN ON AND OFF POSITIONS

[75] Inventors: Katsushi Watanabe; Takashi Suzuki, both of Hachioji; Kazutaka Matsumoto, Fuchu, all of Japan

[73] Assignee: Olympus Optical Co., Ltd., Japan

[21] Appl. No.: 09/152,572

[22] Filed: Sep. 14, 1998

[30] Foreign Application Priority Data

Sep. 18, 1997 [JP] Japan ..................................... 9-253770
Aug. 5, 1998 [JP] Japan ................................... 10-221915

[51] Int. Cl.[7] ....................................................... A61B 1/06
[52] U.S. Cl. ........................................... 600/178; 600/160
[58] Field of Search ..................................... 600/178, 179, 600/160, 131, 132, 198, 199

[56] References Cited

U.S. PATENT DOCUMENTS

| | | | |
|---|---|---|---|
| 3,315,207 | 4/1967 | Speelman | 600/199 |
| 3,592,199 | 7/1971 | Ostensen | 600/198 |
| 5,060,633 | 10/1991 | Gibson | 600/199 |
| 5,170,775 | 12/1992 | Tagami | 600/178 |
| 5,178,131 | 1/1993 | Upsher | 600/199 |
| 5,588,950 | 12/1996 | Sano et al. . | |
| 5,924,978 | 7/1999 | Koeda et al. | 600/131 |

FOREIGN PATENT DOCUMENTS 9224906  9/1997  Japan .

Primary Examiner—John P. Leubecker
Attorney, Agent, or Firm—Ostrolenk, Faber, Gerb & Soffen, LLP

[57] ABSTRACT

An endoscope apparatus includes an endoscope having a light guide fiber for guiding illumination light and a battery-powered light source detachably mounted on the endoscope. A lamp in the light source is switched between a turned-on state and a turned-off state by changing a relative position between the battery-powered light source and the endoscope while the battery-powered light source is mounted on the endoscope. With this arrangement, it can be easily discerned whether the lamp is turned on or off from a glance at the outside appearance of the endoscope apparatus.

19 Claims, 18 Drawing Sheets

FIG.25A FIG.25B

ENDOSCOPE APPARATUS HAVING LIGHT SOURCE MOVABLE BETWEEN ON AND OFF POSITIONS

BACKGROUND OF THE INVENTION

1. Field of the Invention

The present invention relates to an endoscope apparatus suitable for portable use.

2. Related Art Statement

Endoscopes have been widely used in the medical field and the industrial field. An object to be diagnosed or examined by the endoscopes is located in the interior of a living body, a plant or the like. Thus, the endoscopes must be provided with illumination means for supplying illumination light thereto.

An ordinary endoscope apparatus comprises an endoscope and an external light source. A lamp is disposed in the light source device and the illumination light emitted from the lamp is guided to a light guide fiber disposed in the endoscope. Then, the illumination light is transmitted through the light guide fiber, emerges from an illumination window disposed on the distal end of an insertion tube and illuminates an object to be examined.

The light source device ordinarily causes the lamp disposed therein to emit light using power supplied form a wall outlet. On the other hand, Japanese Unexamined Patent Publication No. 9-224906, for example, discloses an endoscope using a battery or the like as the power supply.

In the endoscope, a battery-powered light source is detachably mounted on a control section of the endoscope. Since the endoscope having the detachably mounted battery-powered light source can be easily carried as well as used in a location where a wall outlet is not readily available, this type of endoscope is suitable for emergency use and the like.

In the battery-powered light source which uses the battery as the power supply for the light source device of the endoscope, however, the lamp is turned on and off by a switch connected to the main body of the light source. Since the switch is generally either a small rotary type knob switch or a push type button switch, it is difficult to discriminate whether the switch is turned on or off at a glance, whereby it would be easy to forget to turn off the switch.

Further, when the endoscope is held by being suspended from an endoscope hanger, the distal end of the endoscope points downward. As a result, when the endoscope is suspended from the hanger with its lamp turned on, it is possible that the endoscope would be kept in that state for an unnecessarily long period of time if the user is unaware of the illuminating light being emitted from the distal end of the endoscope. Therefore, the battery would become unusable due to battery exhaustion.

A further disadvantage is encountered if the operator unintentionally turns on the light when preparing the endoscope for use or when washing the endoscope and causing the battery to go dead and therefore unusable.

OBJECTS AND SUMMARY OF THE INVENTION

An object of the present invention is to provide an endoscope apparatus which permits a user to readily determine whether a battery-powered light source is turned on or off upon a glance at the outside thereof.

Another object of the present invention is to provide an endoscope apparatus arranged such that a switch can be turned on only when an operator intends to operate the battery-powered light source.

Briefly described, an endoscope apparatus of the present invention which permits a user to readily determine whether a lamp is turned on or off comprises an endoscope having a light guide fiber for guiding illumination light and a battery-powered light source detachably mounted on the endoscope for switching a lamp between a turned-on state and a turned-off state by changing a relative position between the battery-powered light source and the endoscope when the battery-powered light source is mounted on the endoscope.

BRIEF DESCRIPTION OF THE DRAWINGS

FIG. 1 to FIG. 16 are views describing a first embodiment of the present invention, wherein:

FIG. 1 is a view showing an entire arrangement of an endoscope apparatus;

FIG. 2 is a view showing an arrangement of the distal end surface of an endoscope;

FIG. 3 is a cross-sectional view showing a state in which a battery-powered light source is connected to a light guide connector;

FIG. 4 is a view illustrating a positional relationship when the battery-powered light source is connected to the endoscope;

FIG. 5 is a perspective view illustrating the schematic arrangement of the battery-powered light source;

FIG. 6A to FIG. 6C are perspective views showing an electric conductive material constituting a power supply main body and a lid member, wherein:

FIG. 6A is a perspective view showing a battery accommodating member;

FIG. 6B is a perspective view showing a lamp accommodating holder;

FIG. 6C is a perspective view showing a battery receiving member;

FIG. 7 is a sectional vie showing an arrangement of a lamp unit;

FIG. 8 is a cross-sectional view showing an arrangement of a light source main body;

FIG. 9A and FIG. 9B are views showing the positional relationship between the lamp accommodating holder provided with an insulation ring and a battery, and the operation thereof, wherein:

FIG. 9A is a sectional view showing a lamp-turned-on state;

FIG. 9B is a sectional view showing a lamp-turned-off state;

FIG. 10 is a view showing the positional relationship between an exterior member and a rotation regulating ring and the operation thereof;

FIG. 11A and FIG. 11B are views showing the positional relationship between a contact spring and the lamp accommodating holder and the operation thereof, wherein:

FIG. 11A is a sectional view showing the lamp-turned-on state;

FIG. 11B is a sectional view showing the lamp-turned-off state;

FIG. 12A and FIG. 12B are views showing the relationship among the rotation regulating engagement portion of the battery accommodating member and the battery receiving member, the exterior member and a lid exterior member, wherein:

FIG. 12A is a sectional view showing a state in which the battery accommodating member is integrally disposed in a battery accommodating unit by the rotation regulating engagement portion;

FIG. 12B is a sectional view showing a state in which the battery receiving member is integrally disposed in the lid exterior member by the rotation regulating engagement portion;

FIG. 13A to FIG. 13C are views illustrating the positional relationship of the battery-powered light source to the control section of the endoscope, wherein:

FIG. 13A is a view when the lamp-turned-on state is observed from above the control section;

FIG. 13B is a view when the lamp-turned-off state is observed from above the control section;

FIG. 13C is a view when the positional relationship in the lamp-turned-on state and the lamp-turned-off state is observed from a side of the control section;

FIG. 14 is a view showing an arrangement of a pin receiving unit formed in a connecting ring constituting the light guide connector;

FIG. 15A and FIG. 15B are views showing positioning means for positioning the battery-powered light source when it is connected to the light guide connector, wherein:

FIG. 15A is a view showing a state in which two positioning pins are disposed in a connecting portion;

FIG. 15B is a view showing a state in which one positioning pin is disposed in the connecting portion;

FIG. 16 is a view showing a state in which the lamp unit is removed from the light source main body, and in which the battery-powered light source is connected to the endoscope.

FIG. 17 and FIG. 18 are views illustrating the relationship between the endoscope apparatus and an endoscope hanger, wherein:

FIG. 17 is a view showing the endoscope hanger for holding the endoscope apparatus;

FIG. 18 is a view showing a state in which the endoscope apparatus is held by the endoscope hanger.

FIG. 19 to FIG. 23 are views showing a second embodiment of the present invention, wherein:

FIG. 19 is a view showing a state before a battery-powered light source is connected to an endoscope control section;

FIG. 20 is a view illustrating the positional relationship of a battery-powered light source to the control section of an endoscope in a lamp-turned-off state when the battery-powered light source is connected to the endoscope control section;

FIG. 21 is a view illustrating the positional relationship of a battery-powered light source to the control section of an endoscope in a lamp-turned-on state when the battery-powered light source is connected to the endoscope control section;

FIG. 22 is a cross-sectional view showing an internal arrangement of the battery-powered light source in the lamp-turned-off state;

FIG. 23 is a cross-sectional view showing the internal arrangement of the battery-powered light source in the lamp turned-on state.

FIG. 24 and FIG. 24 are views illustrating a third embodiment of the present invention, wherein:

FIG. 24 is a view illustrating the positional relationship of a battery-powered light source to an endoscope control section in a lamp-turned-on state;

FIG. 25A and FIG. 25B are views illustrating the positional relationship of the battery-powered light source in a lamp-turned-off state, wherein:

FIG. 25A is a view illustrating the positional relationship of the battery-powered light source to the endoscope control section; and FIG. 25B is a view when the battery-powered light source of FIG. 25A is observed from the side of an arrow 25B.

DESCRIPTION OF THE PREFERRED EMBODIMENTS

A first embodiment of the present invention will be described with reference to FIG. 1 through FIG. 18.

Figure 1:
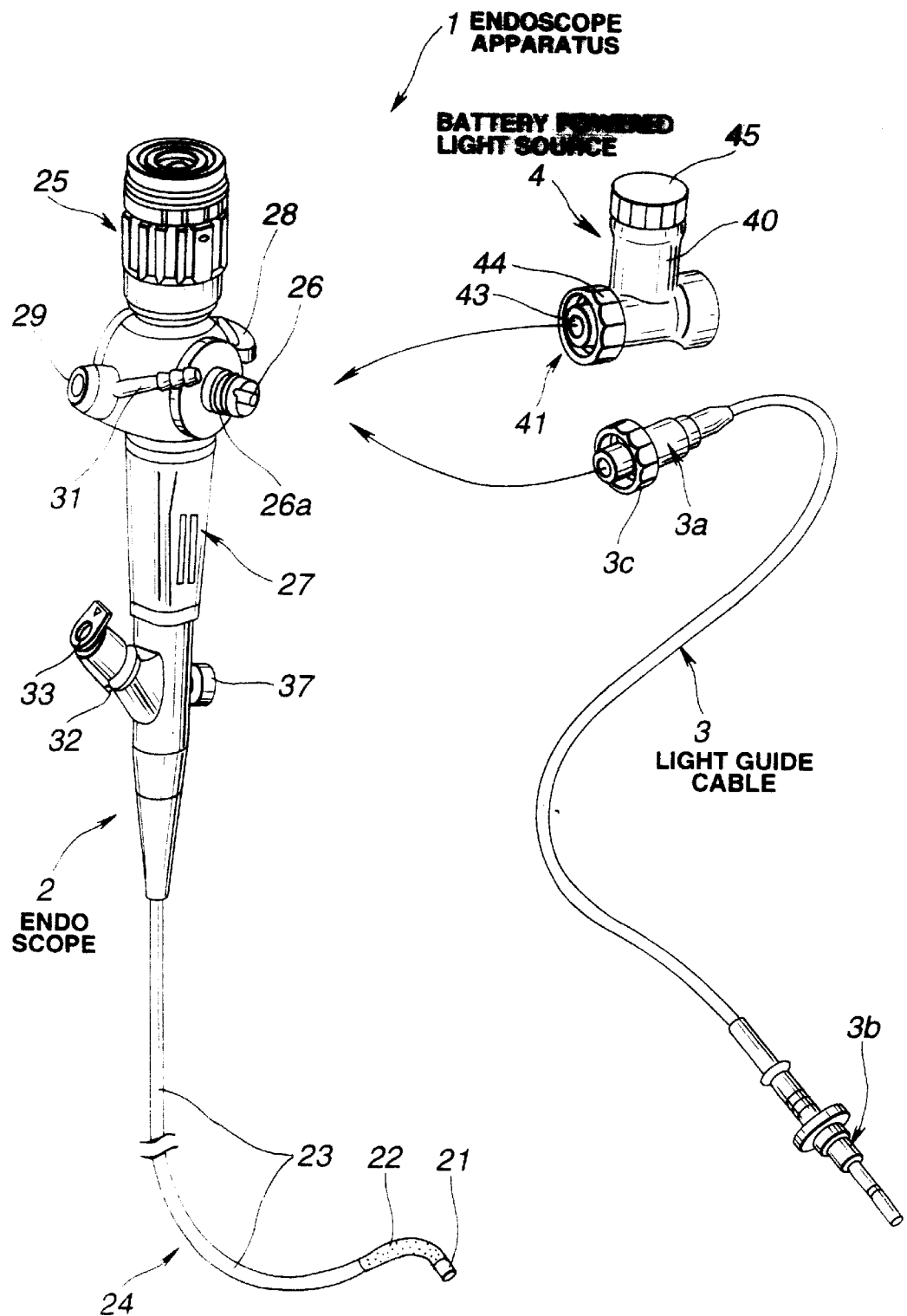

As shown in FIG. 1, an endoscope apparatus 1 of the present invention comprises a water-tight endoscope 2, a light guide cable 3 and a water-tight battery-powered light source 4.

The endoscope 2 includes a distal end portion 21, a bending section 22 which can be bent toward an intended direction, a slender insertion tube 24 formed substantially by flexible tube portion 23, a control section 27 located at the proximal end of the insertion tube 24, an eyepiece section 25 disposed on the proximal end of control section 27, and a light guide connector 26 projecting from a side of the control section 27 and composed of a material having good thermal conductivity. The foregoing components are sequentially disposed from the distal end of the endoscope 2. Further, the control section 27 also serves as a gripping area for the endoscope 2.

The light guide cable 3 is detachably connectable to the light guide connector 6 disposed on the control section 27 of the endoscope 2 through a connecting unit 3a.

The battery-powered light source 4 comprises a lamp and a battery which will be described later. The battery-powered light source is approximately T-shaped. The battery-powered light source 4 is detachably connectable to the light guide connector 26 through a connecting unit 41. The light guide cable 3 and the battery-powered light source 4 are selectively and alternatively connectable to the control section 27.

An angulation control lever 28 is disposed on the control section 27 so that the bending section 22 can be bent by the operation of the angulation control lever 28.

The control section 27 includes a suction button 29 for carrying out a suction operation and a suction connector 31 projecting in a radial direction from the face of the suction button 29 and which communicates with a suction channel 30 (see FIG. 2) extending through the endoscope 2. The suction connector 31 is connectable to a suction device (not shown) through a tube (not shown). Proper operation of the suction button 29 permits the body fluids in a body cavity to be sucked through the suction channel 30 and the suction connector 31.

Further, a port 32 into which an endoscopic treatment instrument such as a biopsy forceps or the like can be inserted is formed near the distal end of the control section 27. The biopsy port 32 communicates with the suction channel 30 extending through the endoscope 2. A biopsy valve 33 is attached to the biopsy port 32.

A light guide fiber 34 (see FIG. 2 and FIG. 3) is inserted into the insertion tube 24 to transmit illumination light. The proximal end of the light guide fiber 34 extends through the control section 27 and is fixed in the light guide connector 26.

Figure 2:
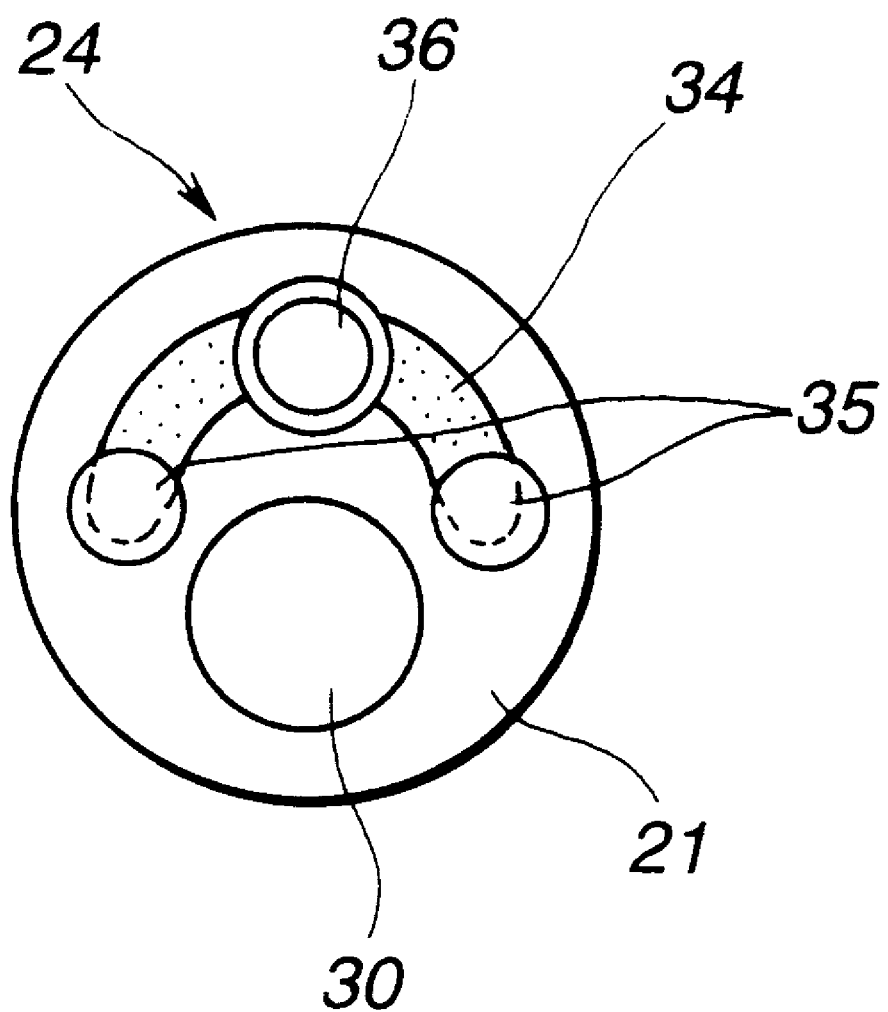

As shown in FIG. 2, the light guide fiber 34 is approximately U-shaped at the distal end portion 21. Illumination windows 35 are provided with a wide illuminating lens and are disposed at both ends of the U-shape of the light guide fiber 34. With this arrangement, the amount of illumination light can be increased by increasing the number of light guide bundles provided to the distal end portion 21. Similarly, the illumination range can be increased by illuminating the illumination light through the illumination windows 35 disposed at both ends of the fiber.

Figure 3:
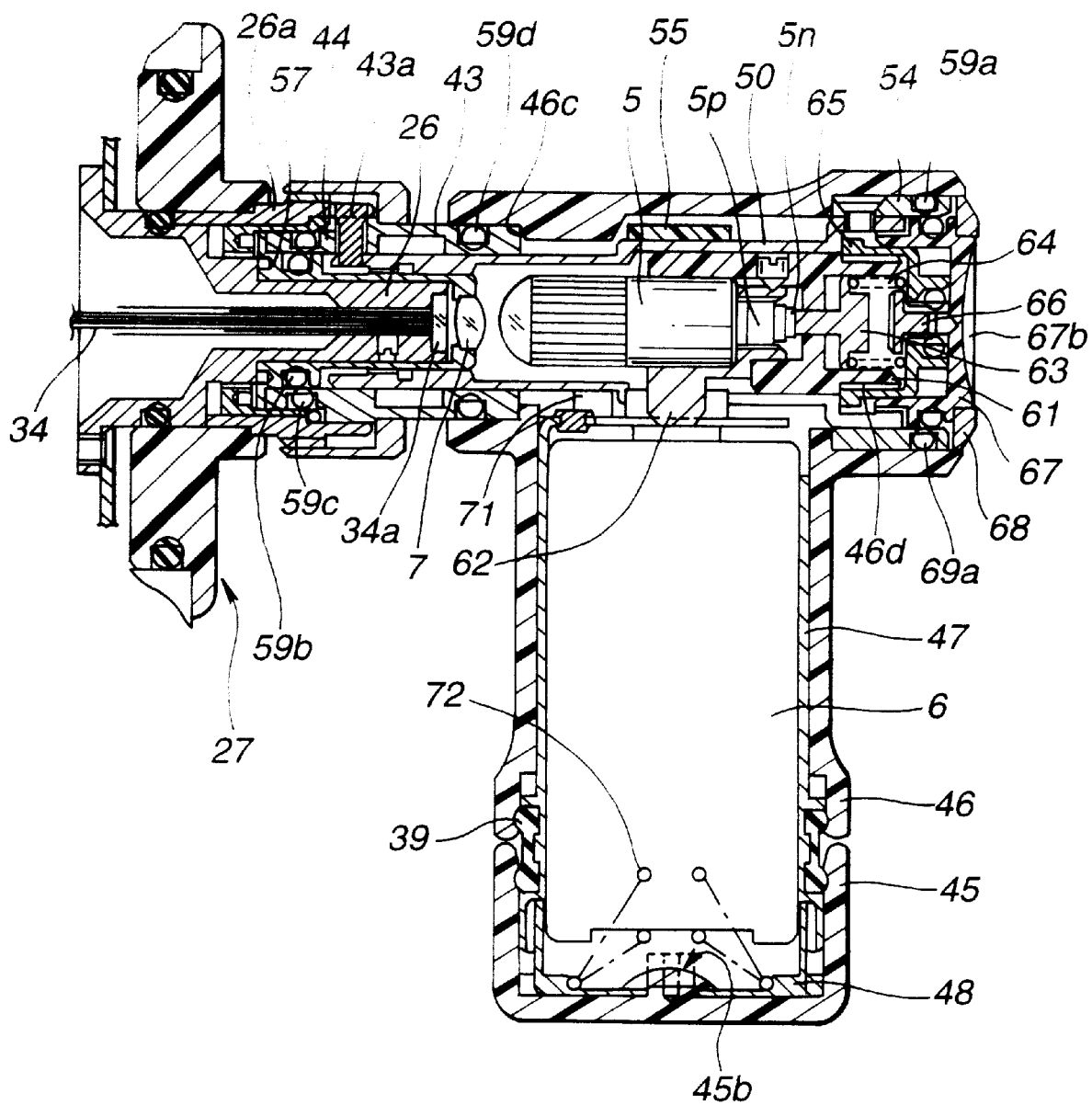

As shown in FIG. 3, the battery-powered light source 4 is connected to the light guide connector 26. When the lamp 5 disposed in the battery-powered light source 4 emits light, the illumination light emitted from the lamp 5 is supplied to a light guide fiber 34 through a light guide fiber glass 34a disposed on the light incident end of the light guide fiber 34 and on the corresponding surface of the light guide connector 26.

Then, the illumination light guided by the light guide fiber 34 is caused emerge from the light guide fiber 34 forming approximately a U-shape as shown in FIG. 2 and through the illumination windows 35 located at the distal end surface of the light guide fiber 34 to thereby illuminate an object to be examined.

The object illuminated by the illumination light forms an optical image at its imaging position through an objective lens system mounted on an observation window 36 disposed in the vicinity of the illumination windows 35. The optical image focused at the imaging position is transmitted to the eye piece section 25 through an image guide fiber, not shown, and observed by a surgeon as an enlarged image through an eyepiece provided to the eye piece section 25.

A ventilating connector 37 projects from the control section 27 of the endoscope 2 at a position opposite to, for example, the biopsy port 32. Any water leakage from the endoscope 2 is checked by supplying air into the endoscope 2 through the ventilating connector 37.

Further, a male screw portion 26a formed in the light guide connector 26 is screwed into a female screw portion formed on the inner surface of a connecting socket 3c which is rotatably disposed on the outer surface of the connecting unit 3a or a female screw portion formed on the inner surface of a connecting socket 44 which is rotatably disposed on the outer surface of the connecting portion 43 of the connecting unit 41. The endoscope 2 is connected to the light guide cable 3 or the battery-powered light source 4 integrally therewith by being screwed thereinto and fixed thereto.

Figure 4:
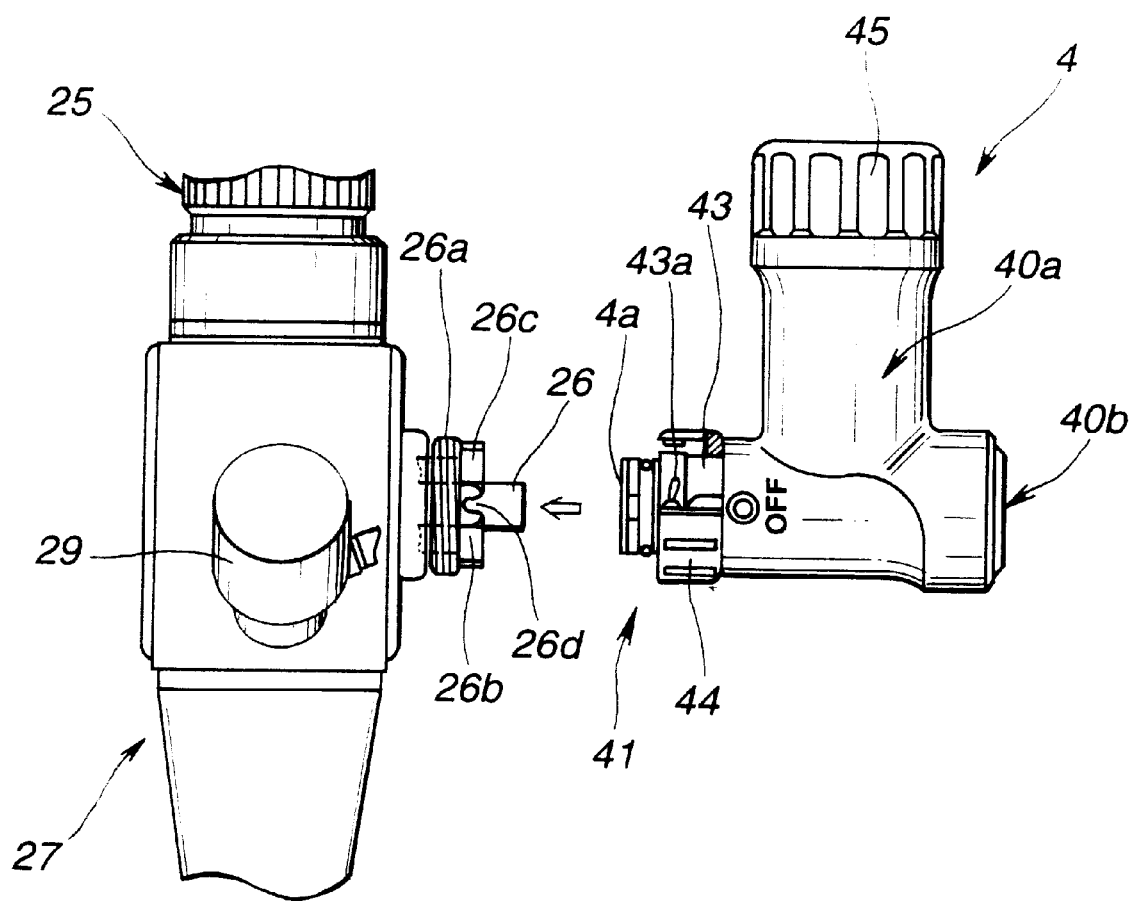

As shown in FIG. 4, when the endoscope 2 is to be coupled with the battery-powered light source 4, an index 26b disposed on the connection ring 26c of the light guide connector 26 is aligned with an index 4a disposed to the battery-powered light source 4, whereupon the battery-powered light source 4 can then be attached to the light guide connector 26. With this operation, the endoscope and the light source are positioned and joined so as to establish a prescribed positional relationship therebetween in such a manner that a positioning pin 43a disposed on the battery-powered light source 4 is inserted into a pin receiving portion 26d disposed on the connection ring 26c of the light guide connector 26.

Figure 15A:
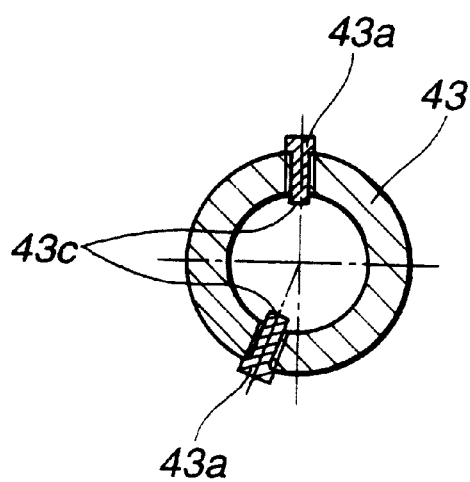
Figure 15B:
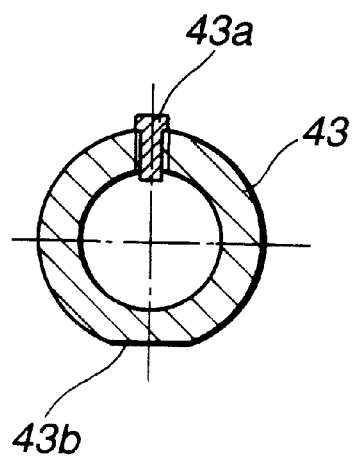

The positioning pin 43a is placed under a significant amount of tension when the battery-powered light source 4 is rotated with respect to the endoscope 2. Accordingly, a plurality of positioning pins 43a are provided on connecting portion 43 as shown in FIG. 15A, while similarly providing a plurality of pin receiving portions 26d on the connection ring 26c to correspond with the positioning pins 43a to thereby disperse the stress and improve strength. Alternatively, a rotation regulating flat portion 43b which is engagable with the connection ring 26c of the light guide connector 26 is formed on the outer surface of the connecting portion 43 as shown in FIG. 15B.

When a plurality of positioning pins are provided the battery-powered light source 4 can be prevented from being reversely assembled to the endoscope 2 by positioning the positioning pins asymmetrically on connecting portion 43, as shown in FIG. 15A.

Once properly aligned, the male screw portion 26a of the light guide connector 26 is screwed into the female screw portion formed on the inner surface of the connecting socket 44 to thereby couple the endoscope 2 to the battery-powered light source 4. As coupled in this manner, the battery-powered light source 4 is turned off so that the lamp 5 is not turned on.

A light guide cable connector 3b provided at the distal end of the light guide cable 3 is connectable to an existing light source device, not shown. When the light guide cable connector 3b is connected to the light source device, the illumination light from a lamp disposed in the light source device is supplied to the light guide fiber 34 of the endoscope 2 through the light guide cable connector 3b, an unillustrated light guide fiber in the light guide cable 3 and the connecting unit 3a.

A lid member 45 is detachably mounted on the battery-powered light source 4, whereby the removal of the lid member 45 permits a battery 6 (see FIG. 5) to be replaced.

An arrangement of the battery-powered light source 4 which is detachably attachable to the light guide connector 26 of the endoscope 2 through the connecting socket 44 will now be described.

Figure 5:
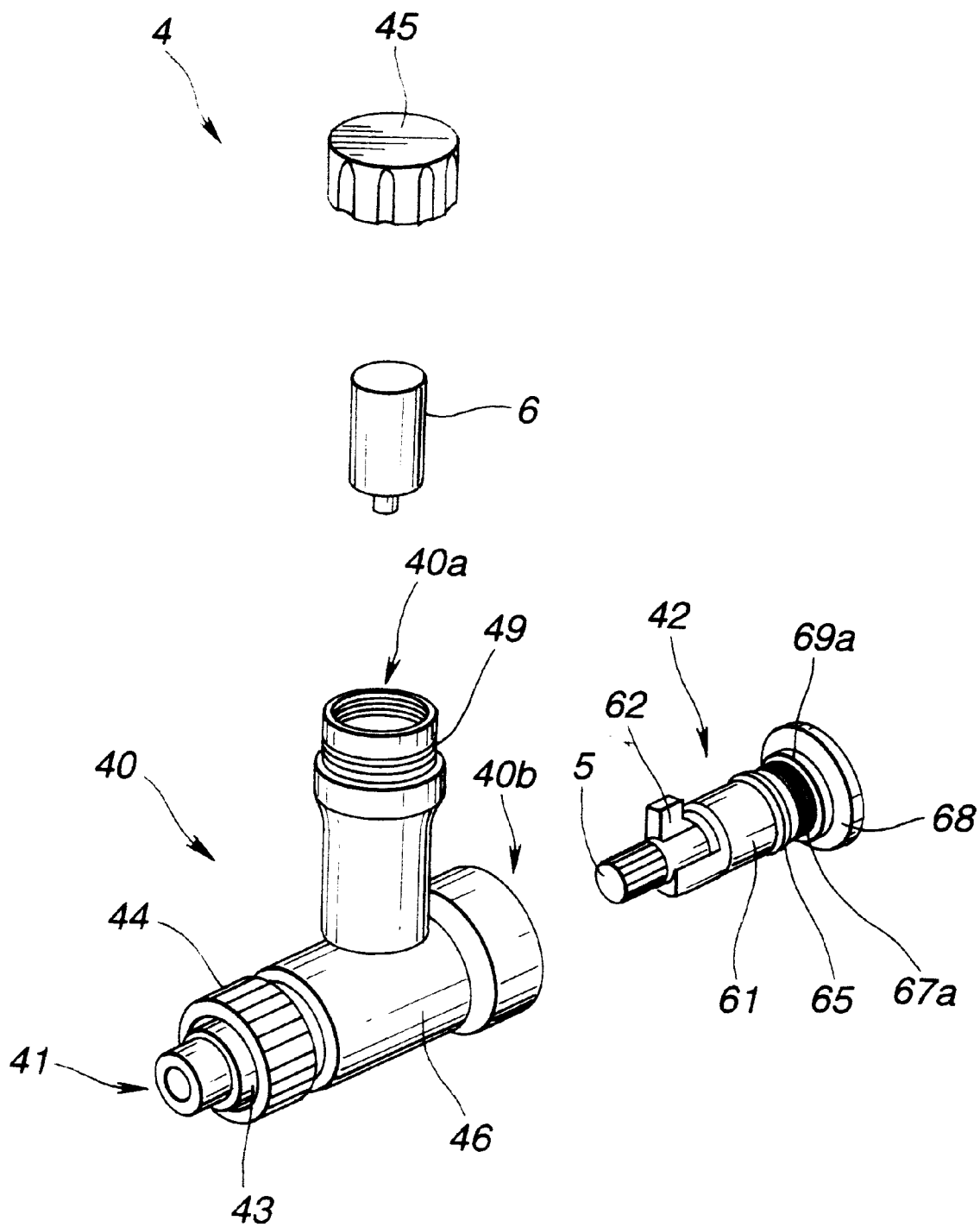

As shown in FIG. 5, the battery-powered light source 4 is composed of a light source main body unit 40, the lid member 45 detachably mounted on the light source main body unit 40 and a lamp unit 42. The battery 6 and the lamp 5 can be replaced by removing the lid member 45 and the lamp unit 42 from the light source main body unit 40, respectively.

Figure 6A:
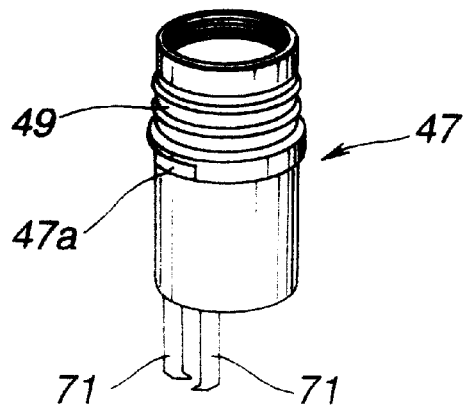
Figure 6B:
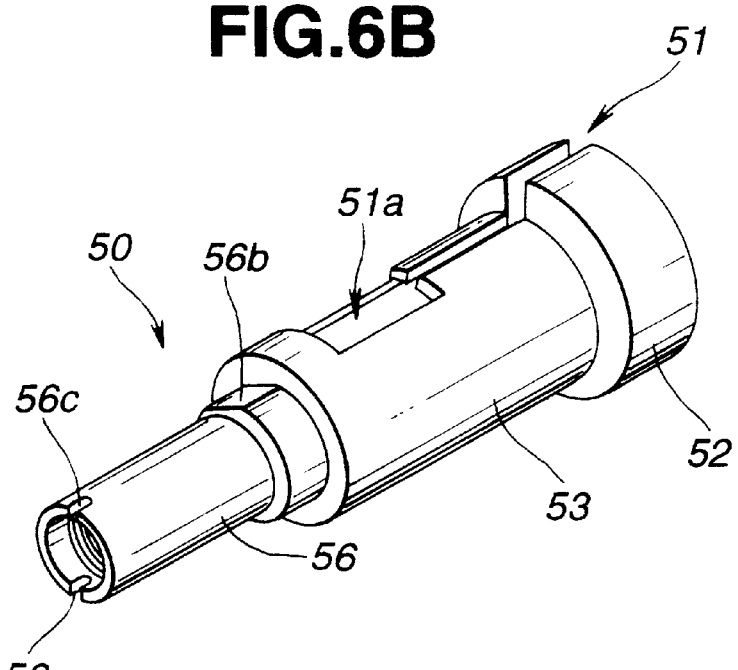
Figure 6C:
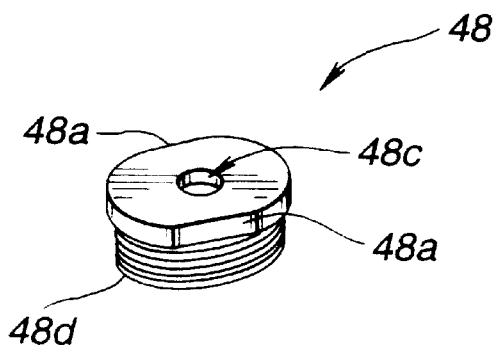

The light source main body unit 40 is mainly composed of an exterior member 46 formed of an insulating resin material, a battery accommodating member 47 disposed on the inner surface of the battery accommodating unit 40a for accommodating the battery 6 and formed of an electrically conductive material as shown in FIG. 6A, and a lamp accommodation holder 50 disposed on the inner surface of a lamp accommodating unit 40b for accommodating the lamp unit 42 and formed of an electrically conductive material as shown in FIG. 6B.

Numeral 49 shown in FIG. 6A is a packing member. Numeral 71 denotes contact springs which will be described later. A battery receiving member 48 shown in FIG. 6C and formed of an electric conductive material is disposed on the inner surface of the lid member 45.

Figure 7:
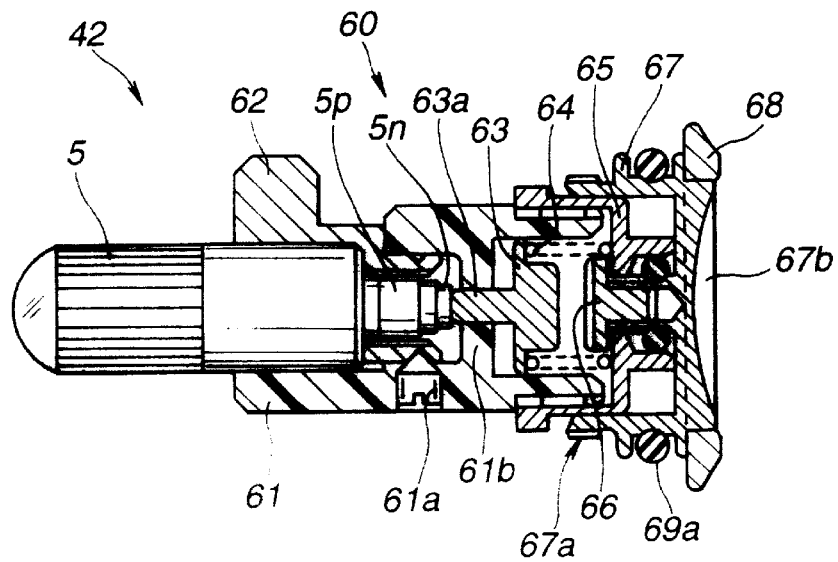

As shown in FIG. 7, the lamp unit 42 is composed of the detachable lamp 5 and a lamp holder 60 on which the lamp 5 can be mounted. A glass surface at the distal end of the lamp 5 is formed to a lens shape for converging an emitted light beam.

The lamp holder 60 is composed of an approximately pipe-shaped holder main body 61, a convex electrical contact portion 62 which is in electrical contact with a lamp side electrode 5p disposed on the side surface of the base end portion of the lamp 5 and which is also in electrical contact with the battery 6 accommodated in the battery accommodating unit 40a, a contact pin 63 having a projection 63a which is loosely engaged with a through hole disposed in a partition 61b formed in the transparent hole of the holder main body 61 and which also has a cross section formed to an approximately "T" shape and formed of an electrically conductive material, an electrically conductive contact spring 64 for urging the contact pin 63 against the lamp rear end electrode 5n, a contact spring receiver 65 covering the base end portion of the holder main body 61 with its outer surface projecting from the outer surface of the holder main body 61 and formed of an electrically conductive material and abutted against the lamp accommodation holder 50, a lamp holder mounting screw portion 67 rotatable with respect to the contact spring receiver 65 through a removal preventing pin 66, and a holder exterior member 68 attached to the lamp holder mounting screw portion 67.

The holder main body 61 is formed of an insulating resin material or the like. The convex electrical contact 62 is fixed to the holder main body 61 by a fixing screw 61a. The distal end surface of the projection 63a is in electrical contact with the lamp rear end electrode 5n disposed on the base end rear surface of the lamp 5. The lamp holder 60 is attached to the lamp accommodation holder 50. A male screw portion 67a is formed on the outer surface of the lamp holder mounting screw portion 67. Further, the holder exterior member 68 is formed of a resin or the like having low thermal conductivity.

A nickel-plated copper alloy is suitable for forming the battery receiving member 48, the battery accommodating member 47, the contact springs 71, the lamp accommodation holder 50, the contact spring receiver 65, the contact pin 63 and the convex electric contact 62. A steel wire which is plated with copper and further plated with nickel is suitable for forming the contact spring 64.

A water-tight ring 69a is disposed on the outer surface of the lamp holder mounting screw portion 67.

Further, a slit 67b is formed on the base end surface of the lamp holder mounting screw portion 67 to mount and dismount the lamp holder.

The lamp accommodation holder 50 is disposed in the lamp accommodating unit 40b of the exterior member 46. As shown in FIG. 6B, the lamp accommodation holder 50 has an approximately slender pipe shape having a plurality of steps formed thereon. An axially extending cutout portion 51 is formed in the lamp accommodation holder 50 from a base end surface to a central barrel portion 53 through a base end side large diameter portion 52. The convex electrical contact 62 included in the lamp unit 42 is inserted through the cutout portion 51. For this purpose, the width of the cutout portion 51 is made larger than that of the convex electric contact 62.

Figure 8:
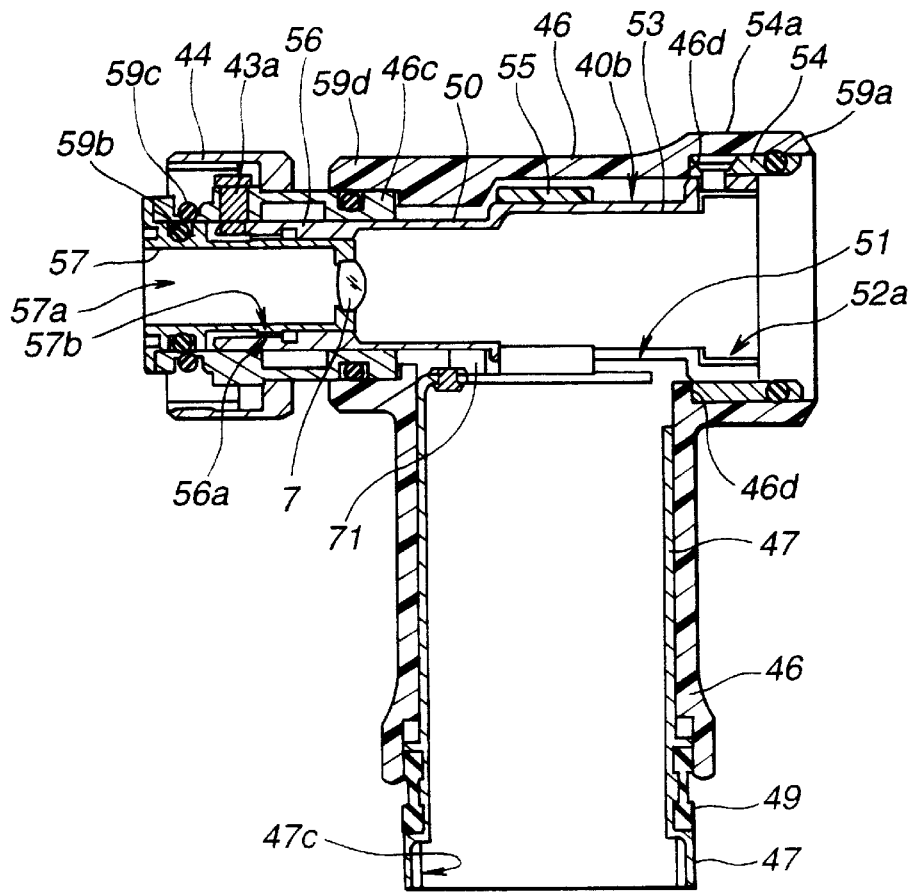

As shown in FIG. 8, a female screw portion 52a is formed on the inner surface of the base ends side large diameter portion 52 of the lamp accommodation holder 50 so that the male screw portion 67a formed on the outer surface of the lamp holder mounting screw portion 67 can be screwed thereinto.

On the other hand, a rotation regulating ring 54 is fixed to the outer surface of the base end side large diameter portion 52 by a screw 54a. The rotation regulating ring 54 is disposed in the lamp accommodating unit 40b. A water-tight ring 59a is disposed on the outer surface of the rotation regulating ring 54. The rotation regulating ring 54 and the lamp accommodating unit 40b are kept in a water-tight state by the water-tight ring 59a.

Figure 9A:
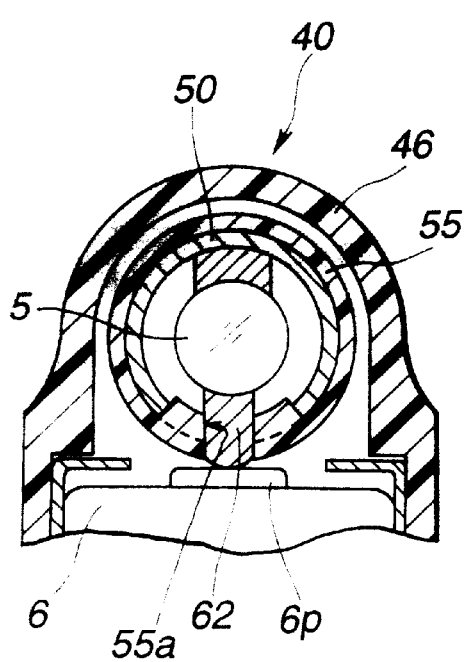
Figure 9B:
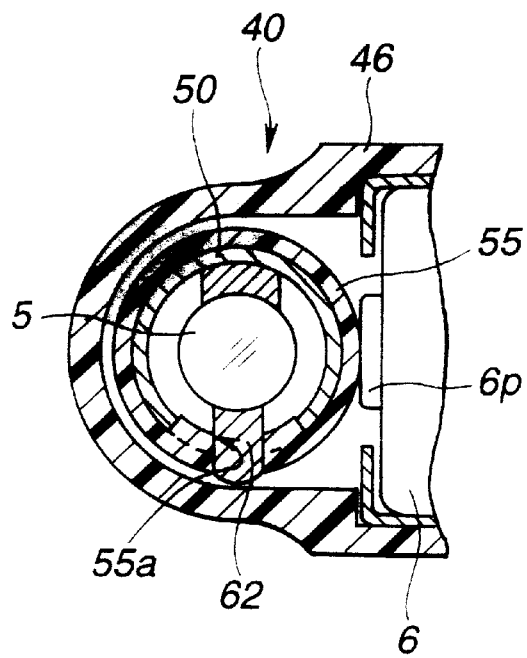

An enlarged opening portion 51a formed at the distal end side of the cutout portion 51 is formed on the central barrel portion 53 of the lamp accommodation holder 50 (see FIG. 6B). As shown in FIGS. 9A and 9B, an insulation ring 55 is disposed on the outer surface of the central barrel portion 53 including the enlarged opening portion 51a. A projection disposing groove 55a having a width approximately as large as that of the cutout portion 51 is formed in the insulation ring 55.

A connecting portion 43 is disposed on the outer surface of the small diameter barrel portion 56 at a position nearer to the distal end of the lamp accommodation holder 50 than the central barrel portion 53 so as to be located in the lamp accommodating unit 40b. A mouthpiece connecting portion 57 having a mouthpiece insertion tube 57a into which the light guide connector 26 is inserted is disposed on the inner surface of the small diameter barrel portion 56. As shown in FIGS. 15A and 15B, the positioning pins 43a are fixed to the connecting portion 43 by screws so that they project inwardly of the connecting portion 43.

The connecting portion 43 is slidingly fitted on the small diameter barrel portion 56 of the lamp accommodation holder 50 so that the projecting portions 43c of the positioning pins 43a are inserted into cutout portions 56c formed to the small diameter barrel end of the lamp accommodation holder and further a male screw 57b formed on the outer surface of the mouthpiece connecting portion 57 is screwed into a female screw 56a formed on the inner surface of the small diameter barrel portion 56. With this operation, the connecting portion 43 and the mouthpiece connecting portion 57 are connected to the lamp accommodation holder 50 integrally therewith at the same time.

The lamp accommodation holder 50 is disposed in the lamp accommodating unit 40b of the exterior member 46 in such a positional relationship that abutting surfaces 46c, 46d, which are formed on the inner surface of the exterior member 46, are clamped between an end surface of the connecting portion 43 of the lamp accommodation holder 50 and an end surface of the rotation regulating ring 54. With this arrangement, the exterior member 46 rotates with respect to the lamp accommodation holder 50.

Additionally, the outer surface of the lamp accommodation holder 50 is not in contact with the exterior member 46 when connected in this manner, such that an air layer is formed therebetween so as to prevent a temperature increase of the exterior member 46 when the lamp 5 is turned on.

Figure 10:
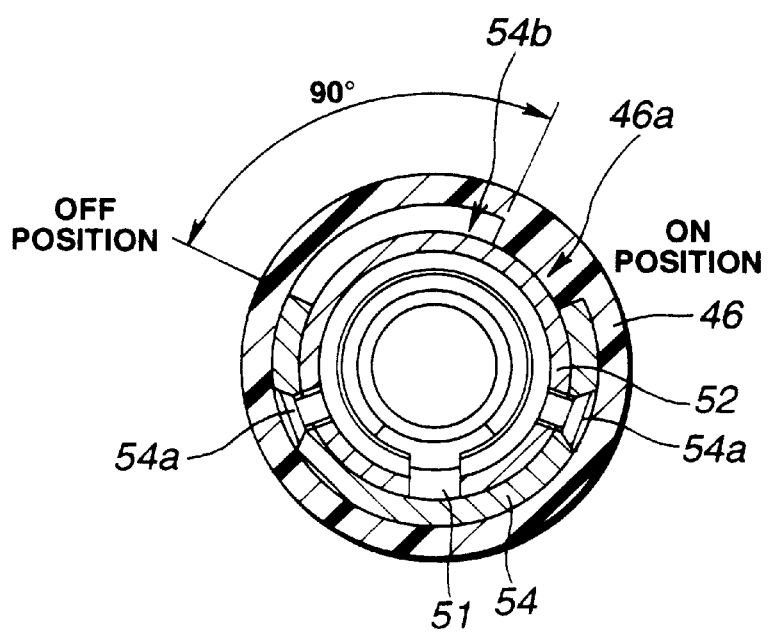

As shown in FIG. 10, the rotation regulating ring 54 disposed on the outer surface of the base end side large diameter portion 52 of the exterior member 46 is approximately C-shaped having a cutout 54b. A convex rotation regulating portion 46a which abuts against the side surface portion of the cutout 54b is disposed on the inner surface of the lamp accommodating unit 40b against which the rotation regulating ring 54 is disposed. The rotational angle of the rotation regulating ring 54 with respect to the exterior member 46 can be set to a desired angle by suitably adjusting the width of the cutout 54b formed in the rotation regulating ring 54. The width in the present embodiment is determined such that the relative rotational angle between the exterior member 46 and the lamp accommodation holder 50 is 90°.

The end on the opening side of the connector connecting portion 57 is inserted into the inner hole of the connecting portion 43. The water-tight state between the outer surface of the mouthpiece connecting portion 57 and the inner surface of the connecting portion 43 is maintained by a water-tight ring 59b disposed on the outer peripheral portion of the connecting portion 57. A converging lens 7 is bonded and affixed to the mouthpiece connecting portion 57 in a water-tight state. Further, a water-tight ring 59c is disposed on the outer surface of the connecting portion 43 to maintain water tightness when it is connected to the endoscope 2. Numeral 59d denotes a water-tight ring disposed on the outer surface of the connecting portion 43. The water tightness between the connecting portion 43 and the lamp accommodating unit 40b is maintained by the water-tight ring 59d.

On the other hand, the battery accommodating member 47 shown in FIG. 6A is disposed on the inner surface of the battery accommodating unit 40a of the light source main body unit 40 for accommodating the battery 6 shown in FIG. 8.

As shown in FIG. 11, the contact springs 71 projecting from the distal end of the battery accommodating member 47 are disposed so as to clamp a portion of the small diameter barrel portion 56 of the lamp accommodation holder 50 which is rotatable with respect to the lamp accommodating unit 40b of the exterior member 46.

As shown in FIG. 11, the small diameter barrel portion 56 clamped by the contact springs 71 has an approximately circular cross section on which a pair of flat portions 56b are formed. The diameter of the small diameter barrel portion 56 is made larger than the interval between the contact springs 71, whereas the width between the pair of flat portions 56b is made approximately equal to the interval between the contact springs 71.

This arrangement permits the circular outer surface of the small diameter barrel portion 56 to come into reliable contact between the contact springs 71 so that when the contact springs 71 are disposed on the flat portions 56b, a click sensation is experienced.

Figure 12A:
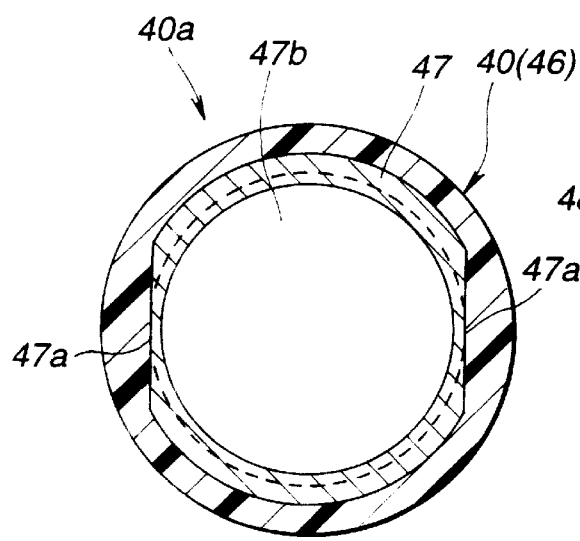
Figure 12B:
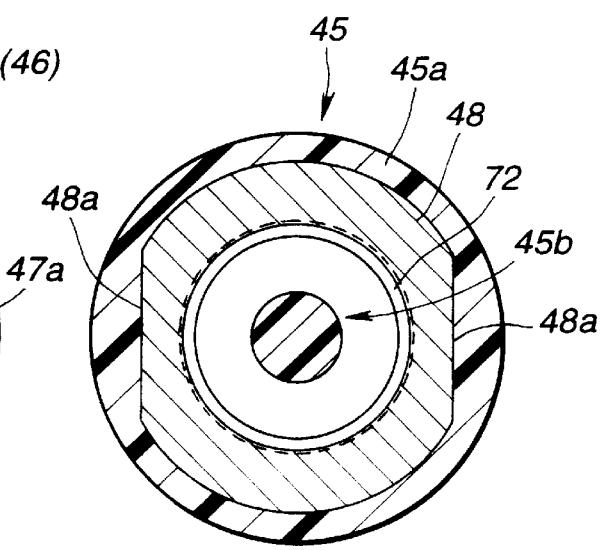

As shown in FIGS. 12A and 12B, rotation regulating engagement portions 47a, 48a are formed on the outer surfaces of the battery accommodating member 47 and the battery receiving member 48 to regulate the rotation between the exterior member 46 and a lid exterior member 45a. The rotation regulating engagement portions 47a, 48a permit the battery accommodating member 47 to be disposed in the battery accommodating unit 40a integrally therewith and also permits the battery receiving member 48 to be disposed in the lid exterior member 45a integrally therewith so that these components are rigidly connected to each other to resist an external force in a rotational direction.

Numeral 47b denotes a battery accommodating space for accommodating the battery 6. Numeral 47c (see FIG. 8) denotes a female screw portion into which a screw portion 48d (see FIG. 6C) formed on the outer surface of the battery receiving member 48 is screwed.

Numeral 45b denotes a caulking portion projecting from the bottom surface of the lid exterior member 45a. After the caulking portion 45b is inserted through a transparent hole 48c formed to the battery receiving member 48, the distal end of the caulking portion 45b is melted by the heat applied thereto by a soldering iron to thereby affix the battery receiving member 48 to the lid exterior member 45a to be integral therewith.

Numeral 72 denotes an electrically conductive spring which is abutted against the negative electrode of the battery 6 and urges the battery 6 against the lamp accommodation holder 50. The spring 72 is fixed to the battery receiving member 48 in an electrically conducting state. A steel wire plated with copper and further plated with nickel is a suitable material for forming the spring 72.

An operation of the battery-powered light source 4 arranged as described above will now be discussed.

First, the battery 6 is placed in the battery accommodating unit 40a of the light source main body unit 40. Thereafter, the battery accommodating unit 40a is covered with the lid member 45 and the screw 48d of the battery receiving member 48 is screwed into the female screw 47c of the battery accommodating member 47 to thereby integrally affix the lid member 45 to the light source main body unit 40. At this time, the packing member 49 disposed on the battery accommodating member 47 comes into intimate contact with the inner surface of the lid member 45 to form a water-tight seal therebetween.

When the relationship between the female screw and the male screw of the battery accommodating member 47 and the lid member 45 and the water-tight seal surface is established as described above, no thread comes into contact with the inner surface (water-tight surface) of the lid exterior member 45a which is formed of a resin or the like and against which the packing member 49 is abutted. Structured as such, the water-tight surface is not damaged even if the lid member 45 is repeatedly mounted and dismounted. Therefore, water tightness can be maintained.

Next, the convex electrically contact 62 of the lamp unit 42 is inserted through the cutout portion 51 of the lamp accommodation holder 50 disposed in the lamp accommodating unit 40b and registered in the projection disposing groove 55a formed in the insulation ring 55. Then, the distal end of a coin or a flathead screwdriver is fitted into the lamp holder mounting/dismounting slit 67b formed in the base end surface of the lamp holder mounting screw portion 67 and is rotated by the coin or flathead screwdriver.

With this operation, the male screw portion 67a formed in the lamp holder mounting screw portion 67 is screwed into the female screw portion 52a formed on the inner surface of the base end side large diameter portion 52, to thereby integrally affix the lamp unit 42 to the light source main body unit 40.

When assembled in this manner, the water-tight ring 69a disposed on the outer surface of the lamp holder mounting screw portion 67 comes into intimate contact with the inner surface of the rotation regulating ring 54 so that a water-tightstate is established therebetween. Further, an air layer is formed between the lamp 5 and the lamp accommodation holder 50 to prevent the direct transmission of heat generated when the lamp 5 is turned on to the lamp accommodation holder 50 as well as to prevent an excessive drop in the lamp temperature.

With the above operation, the negative electrode of the battery 6 is electrically connected to the rear electrode 5n of the lamp 5 at all times through each of the spring 72, the battery receiving member 48, the battery accommodating member 47, the contact springs 71, the lamp accommodation holder 50, the contact spring receiver 65, the contact spring 64 and the contact pin 63 as shown in FIG. 3.

On the other hand, when the cutout portion 51 of the lamp accommodation holder 50 is aligned with the positive electrode of the battery 6 as shown in FIG. 9A, the convex electrical contact 62 located in the groove 551 comes into contact with the positive electrode of the battery 6 so that the positive electrode of the battery 6 becomes electrically connected to the electrode 5p of the lamp 5.

However, when the exterior member 46 is rotated with respect to the lamp accommodation holder 50 to thereby cause the positive electrode of the battery 6 to come into contact with the insulation ring 55 disposed in the lamp accommodation holder 50, an electrically unconductive state is established between the lamp electrode 5p and the positive electrode of the battery 6.

Figure 11A:
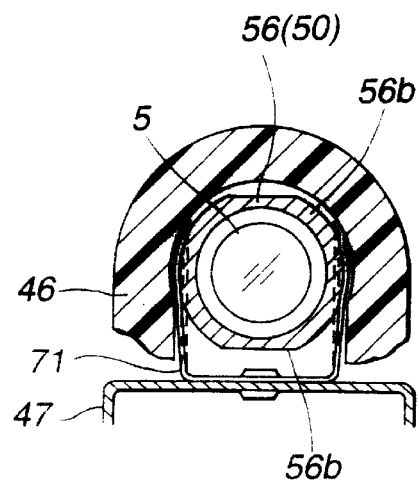
Figure 11B:
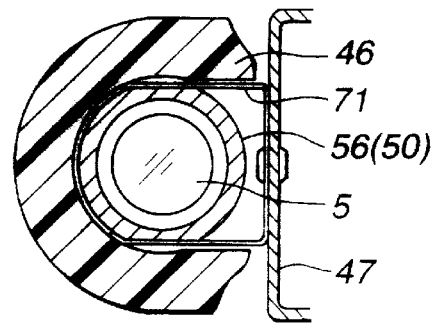
Figure 13A:
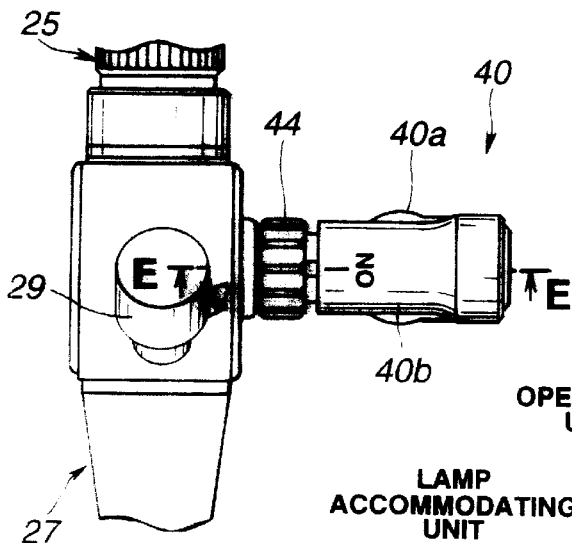
Figure 13C:
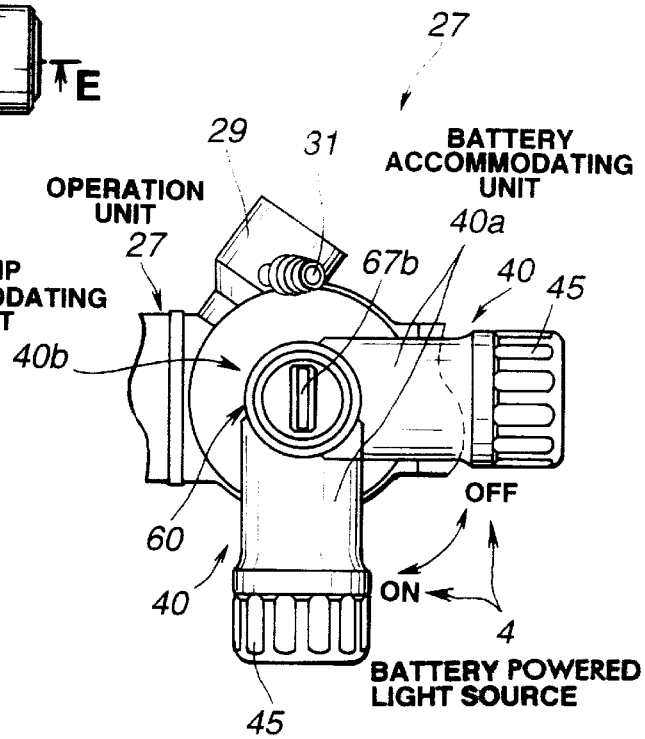
Figure 13B:
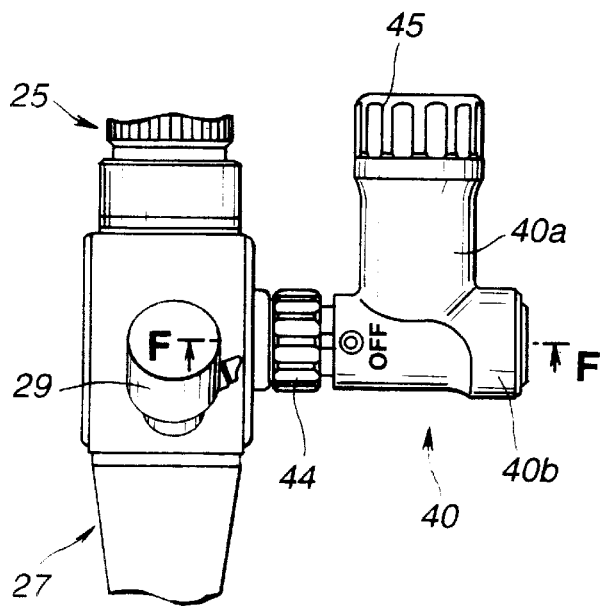

More specifically, when the exterior member 46 of the battery-powered light source 4 is connected to the control section 27 of the endoscope 2 as shown in FIG. 13C and is rotated so that the battery accommodating unit 40 of the light source main body unit 40 is positioned with its axis parallel to the optical axis of the eyepiece section 25 of the control section 27 as shown in FIG. 13B, the positional relationship shown in FIG. 9B and FIG. 11B can be obtained. With this operation, the positive electrode of the battery 6 comes into contact with the insulation ring 55 so that the lamp 5 is not electrically connected to the battery 6 and the lamp 5 is turned off.

On the other hand, when the exterior member 46 of the battery-powered light source 4 is connected to the control section 27 of the endoscope 2 as shown in FIG. 13C and is rotated so that the battery accommodating unit 40a of the light source main body unit 40 is positioned with its axis vertical to the optical axis of the eyepiece section 25 of the control section 27 as shown in FIG. 13A, the positional relationship shown in FIG. 9A and FIG. 11A can be obtained. With this operation, the convex electrical contact 62 comes into contact with the positive electrode of the battery 6, and the negative electrode of the battery 6 is connected to the lamp rear electrode 5n through each of the spring 72, the battery receiving member 48, the battery accommodating member 47, the contact springs 71, the lamp accommodation holder 50, the contact spring receiver 65, the contact spring 64 and the contact pin 63, so that the lamp 5 is turned on by being electrically connected to the battery 6.

As described above, the exterior member of the battery-powered light source is rotated by a prescribed angle with respect to the lamp accommodating holder disposed in the exterior member, whereby the lamp is connected and disconnected to the battery by the rotating operation. Accordingly, the lamp can be turned on and off by rotating the exterior member of the light source main body of the battery-powered light source by 90° with respect to the lamp accommodating holder when the battery-powered light source is attached to the endoscope.

Further, whether the battery-powered light source is turned on or off can be distinguished upon a glance at the positional relationship between the endoscope and the battery-powered light source, such as the positional relationship of the battery accommodating unit of the light source main body of the battery-powered light source with respect to the endoscope control section, or the like. This arrangement can easily prevent a user from forgetting to switch the lamp 5 from a turned-on state to a turned-off state, which in turn would prevent the battery from becoming unusable due to battery exhaustion when it is used next time.

Further, since the battery accommodating unit which occupies a large ratio of the weight of the battery-powered light source is disposed at the periphery of the lamp accommodating holder, the center of gravity of the battery-powered light source can be located as close to the endoscope main body as possible. With this arrangement, the balance of weight of the apparatus can be improved as a whole, and as a result, handling can be improved.

Figure 14:
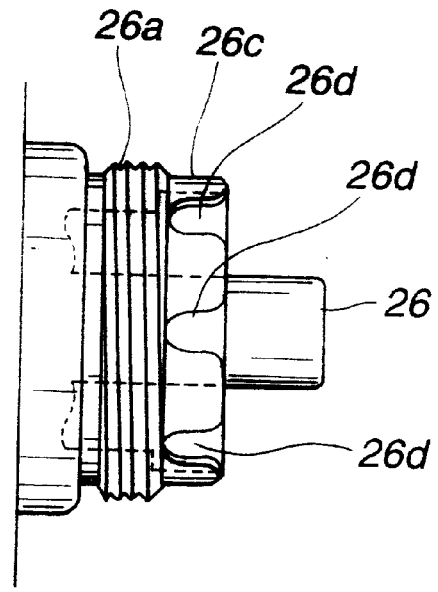

When a plurality of the pin receiving portions 26d, into which the positioning pins 43a provided with the battery-powered light source 4 are disposed, are formed in the connection ring 26c which constitutes part of the light guide connector 26 as shown in FIG. 14, the battery-powered light source 4 can be disposed at a desired angle with respect to the endoscope 2 by selectively combining an arbitrary pin receiving portion 26d with an arbitrary positioning pin 43a.

Figure 16:
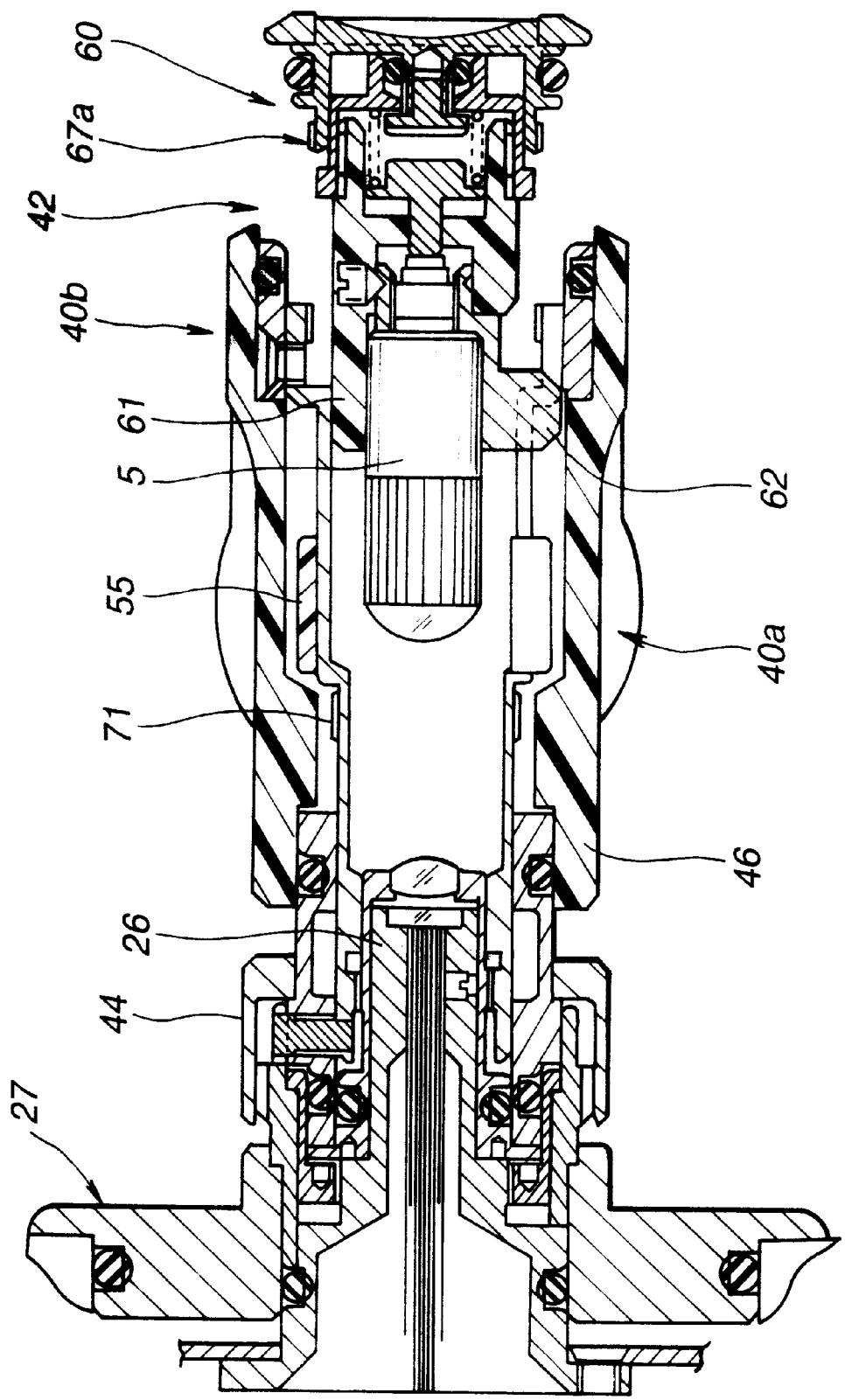

When the positional relationship between the exterior member 46 of the battery type light source 4 and the lamp accommodation holder 50 is in a turned-off state, the lamp 5 can be replaced by removing the lamp unit 42 from the light source main body unit 40 even if the battery-powered light source is connected to the control section 27 of the endoscope 2 as shown in FIG. 16.

Figure 17:
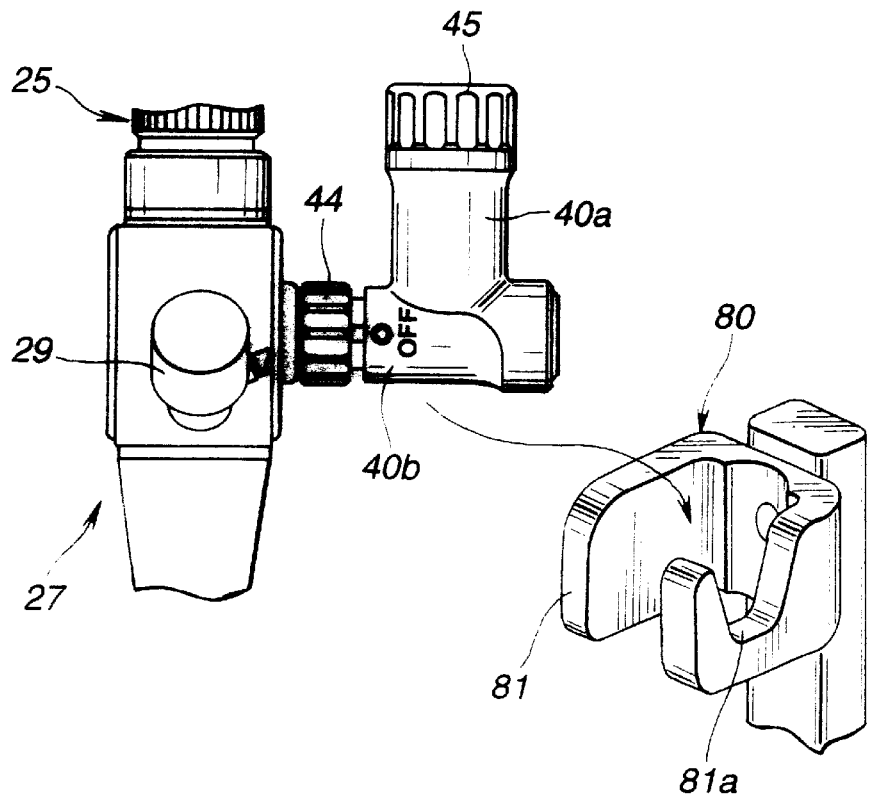
Figure 18:
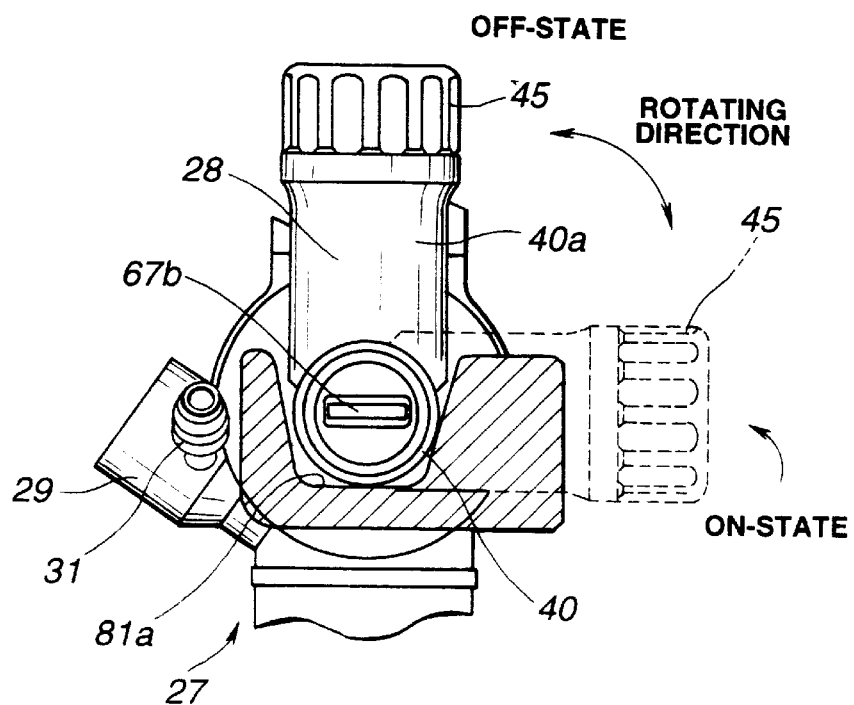

Further, as shown in FIG. 17 and FIG. 18, a battery-powered light source engaging portion 81a is formed in one of the holding members 81 of an endoscope hanger 80 for holding the endoscope apparatus 1 having the battery-powered light source 4 integrally connected to the endoscope 2.

With this arrangement, the lamp accommodating unit 40b can be placed in the battery-powered light source engaging portion 81a only in the turned-off state in which the optical axis of the eyepiece section 25 of the control section 27 is parallel to the axis of the battery accommodating unit 40a of the light source main body unit 40 to thereby permit the endoscope apparatus 1 to be hooked to the endoscope hanger 80. This arrangement prevents the endoscope apparatus 1 from being hooked to the endoscope hanger 80 while the battery-powered source light 4 is still turned on.

A second embodiment of the present invention will be described with reference to FIG. 19 to FIG. 23.

Figure 19:
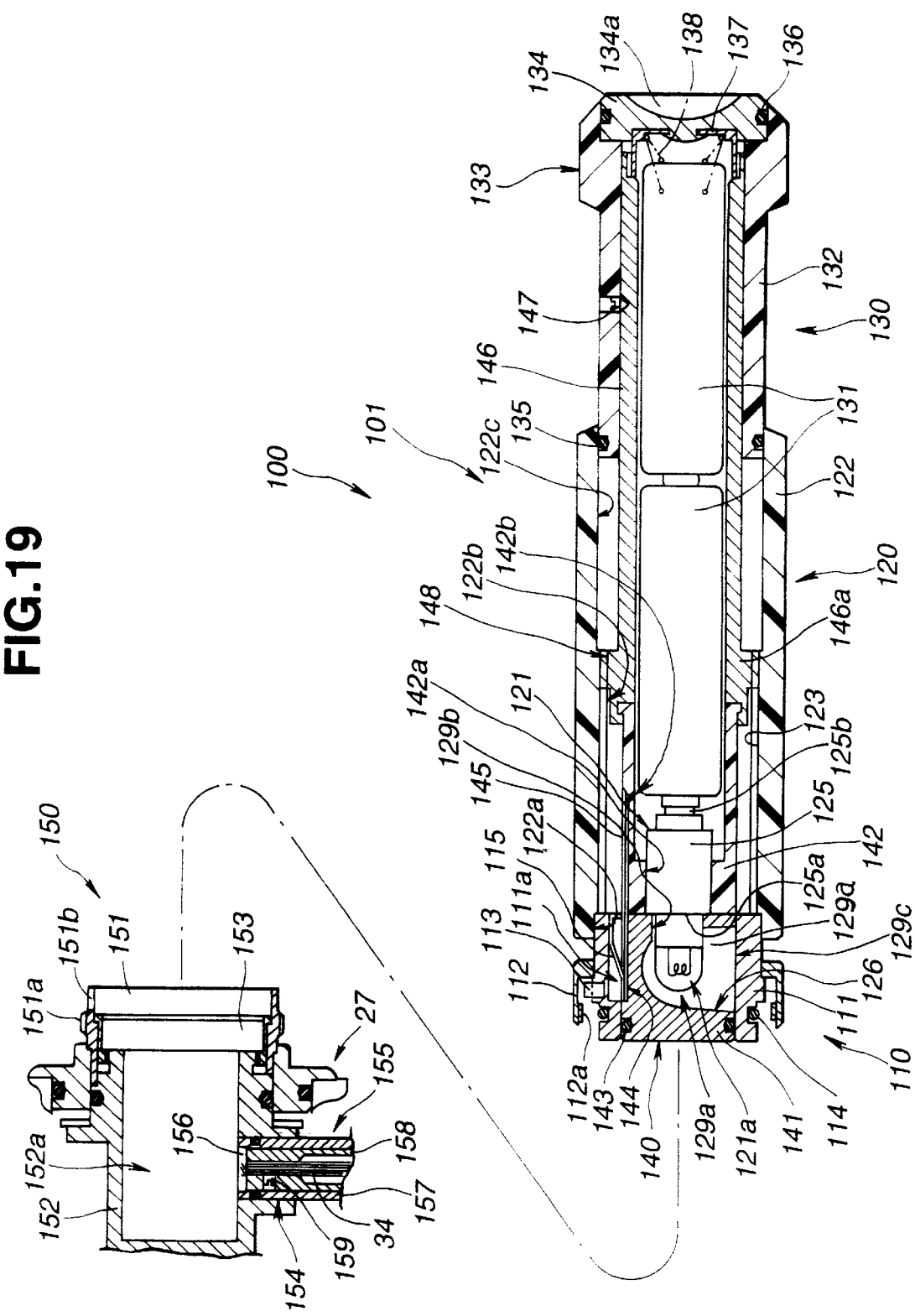

As shown in FIG. 19, in an endoscope apparatus 100 of the embodiment, a battery-powered light source 101 is formed to be approximately I-shaped. The battery-powered light source 101 is composed of a light source main body 120 having a lamp 121 disposed therein and a switch control section 130 having two dry batteries 131 disposed therein.

The battery-powered light source 101 is detachably connected to a battery-powered light source connecting unit 150 in an endoscope control section 27 through a connecting portion 110. The embodiment is arranged such that when the battery-powered light source 101 is connected to the battery-powered light source connecting unit 150 of the endoscope control section 27 through the connecting portion 110, the length of the battery-powered light source 101 is made significantly different depending upon whether the lamp is turned on or turned off as shown in FIG. 20 and FIG. 21.

Figure 20:
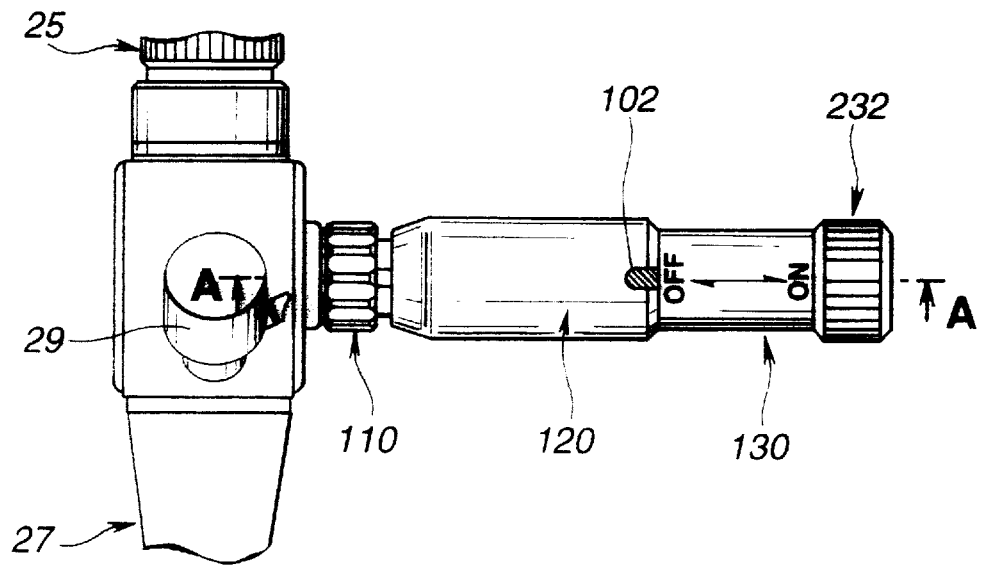
Figure 21:
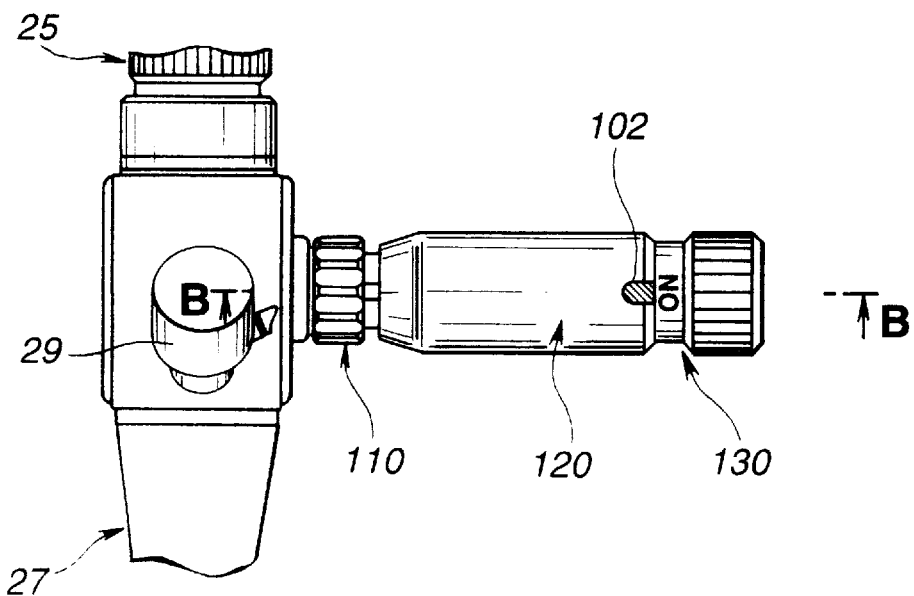

This is because when the lamp is turned off as shown in FIG. 20, the switch control section 130 projects from the light source main body 120 as shown in FIG. 20, whereas when the lamp is turned on as shown in FIG. 21, the switch control section 130 is inserted into the light source main body 120.

Reference numeral 102 denotes an index such that when the switch control section 130 projects from the light source main body 120, the word "OFF" marked on the switch control section 130 is located in the vicinity of the index 102. Similarly, when the switch control section 130 is inserted into the light source main body 120, the word "ON" marked on the switch control section 130 is located in the vicinity of the index 102.

First, an arrangement of the battery-powered light source 101 and an arrangement of the battery-powered light source connecting unit 150 of the endoscope control section 27 will be described with reference to FIG. 19.

As shown in the figure, the battery-powered light source 101 is mainly comprised of the connecting portion 110, the approximately pipe-shaped light source main body 120 and the switch control section 130. The connecting portion 110 is disposed at the distal end of the light source main body 122 which forms the light source main body 120 and is formed of an insulating material. A control section main body 132 which constitutes the switch control section 130 is disposed in the internal hole of the light source main body 122 so as to freely advance and retract therein.

The internal hole of the light source main body 122 is composed of a distal end large diameter portion 122a, a small diameter hole portion 122b and a large diameter hole portion 122c. The small diameter hole portion 122b is formed at the distal end side of the light source main body 122 and has a female screw 123 formed on the inner surface thereof.

On the other hand, the large diameter hole portion 122c is formed at the base end side of the light source main body 122 and the control section main body 132 of the switch control section 130 is inserted into the inner surface of the large diameter hole portion 122c so as to freely advance and retract therein.

The distal end large diameter portion 122a is formed at the distal end of the light source main body 122 and has a diameter approximately as large as that of the large diameter hole portion 122c. An approximately pipe-shaped connecting portion 111 which forms the connecting portion 110 is affixed to the distal end large diameter portion 122a in a water-tightstate. A fixing ring 112 having a female screw 112a formed on the inner surface thereof is rotatably fitted on the connecting portion 111. A positioning pin 113 is screwed onto and fixed to the outer surface of the connecting portion 111, and a water-tight ring 114 is disposed on the outer periphery of the distal end of the connecting ring 111.

A lamp unit 140 is slidably disposed in the inner surface of the connecting portion 111. The lamp unit 140 is composed of a lamp housing 141 formed of an electrically conductive material and an approximately pipe-shaped lamp receiver 142 formed of an insulting material, the lamp housing 141 and the lamp receiver 142 being arranged integrally with each other.

A water-tight ring 143 is disposed on the outer periphery of the distal end of the lamp housing 141 to prevent entry of water from the outside when the lamp is turned off. A groove portion 144 extending in a longitudinal axial direction is formed in the lamp unit 140 in the lamp housing 141 and the lamp receiver 142. An electrically conductive plate 145 is affixed to the bottom of the groove portion 144.

Formed in the lamp housing 141 are a lamp disposing space 129a which the bulb 124 of the lamp 121 is disposed, an introducing hole 129b extending in the longitudinal direction for introducing a part of the bulb 124 and the base 125 of the lamp 121 into the lamp disposing space 129a and a light casting hole 129c opened to the side surface of the lamp housing 141 for casting the light from the bulb 124 to the outside.

The inner surface of the lamp disposing space 129a is mirror-finished so as to act as a reflector surface 126 for converging the light from the lamp 121 in the direction of the light casting hole 129c.

The lamp receiver 142 has a transparent hole including a small diameter hole portion 142a and a large diameter hole portion 142b. The base 125 of the light source lamp 121 is disposed in the small diameter hole portion 142a formed on the distal end side of the lamp receiver 142. The dry batteries 131 serving as the power supply of the light source lamp 121 are partially disposed in the large diameter hole portion 142b formed on the base end side of the lamp receiver 142.

A slender, approximately pipe-shaped battery case 146 formed of an electrically conductive material is rotatably engaged with an outer periphery of the base end portion of the lamp receiver 142.

A cutout portion 111a formed in the longitudinal axial direction is formed on the inner surface of the connecting portion 111. The cutout portion 111a is formed to confront the groove portion 144 of the lamp housing 141. An electrically conductive spring member 115 is fixed to the cutout portion 111a. An end of the spring member 115 is inserted into the groove portion 144 by its elastic force and abutted against the electrically conductive plate 145 fixed to the bottom thereof at all times, whereas the other end thereof has a contact surface formed thereto which serves as an electrical contact with the battery case 146.

When the light source lamp 121 is mounted as show in the figure and the stepped portion 125a of the base 125 forming one of the electrodes of the light source lamp 121 is abutted against the base end surface of the lamp housing 141, the filament portion 121a of the light source lamp 121 is positioned at the focusing position of the reflector surface 126. In this manner, the direction of the light source lamp 121 is positioned with respect to the reflector surface 126 so that the longitudinal direction of the filament portion 121a of the light source lamp 121 coincides with the focusing direction of the reflector surface 126.

On the other hand, the battery case 146 is disposed in the internal hole of the control section main body 132 of the switch control section 130. A battery cap 134 through which the dry batteries 131 and the light source lamp 121 are mounted and dismounted is disposed in the internal hole of the knob portion 133 of the control section main body 132.

The battery case 146 has a space capable of accommodating two batteries in series in the internal hole thereof and is integrally affixed to the inner surface of the control section main body 132 by a fixing screw 147 or the like.

A water-tight ring 135 is disposed on the outer peripheral portion of the distal end of the control section main body 132 to keep a water-tight seal between the control section main body 132 and the large diameter hole portion 122c of the light source main body 122 at all times. Further, a water-tight ring 136 is disposed on the outer peripheral portion of the battery cap 134 to keep a water-tight seal between the battery cap 134 and the control section main body 132.

A battery receiver 137 formed on an electrically conductive material is fixed to the distal end surface of the battery cap 134 integrally therewith. A male screw is formed on the outer surface of the battery receiver 137 and screwed into a female screw formed on the inner surface of the base portion of the battery case 146. In addition, a press spring 138 comprised of a wire having a small electrical resistance and formed in the shape of a frustum of a cone is fixed to the bottom of the battery receiver 137. A slit 134a, into which a coin or the like is inserted, is formed on the base end surface of the battery cap 134.

When the battery cap 134 is disposed in the vicinity of the knob portion 133 and the battery cap 134 is rotated in a prescribed direction by a coin or the like inserted into the slit 134a, the battery receiver 137 fixed to the battery cap 134 integrally therewith is screwed into and affixed to the battery case 146. In this manner, the battery cap 134 is secured to the control section main body 132 in a water-tight state. Further, the dry batteries 131 are urged against the distal end thereof by the urging force of the spring 138 so that the dry batteries 131 are reliably abutted against a lamp rear and electrode 125b.

A peripherally projecting portion 146a is formed around the circumference of the distal end of the battery case 146, while a male screw 148 which is screwed into the female screw 123 formed in the small diameter hole portion 122b of the light source main body 122, is formed on the outer surface of the peripherally projecting portion 146a.

Therefore, when the knob portion 133 is gripped and the control section main body 132 is rotated, the peripherally projecting portion 146a advances and retracts in the small diameter hole portion 122b. With this operation, the control section main body 132 which is arranged integrally with the battery case 146 also advances and retracts with respect to the large diameter hole portion 122c of the light source main body 122.

Since the battery-powered light source 101 is arranged as described above, it has a structure which prevents the invasion of the water thereinto from the outside. The thread pitch of the portion where the male screw 148 is screwed into the female screw 123 is relatively large. Alternatively, a moving mechanism may be arranged by the combination of a cam groove having a large pitch and a pin to be inserted into the cam groove in place of the moving mechanism comprised of the female screw 123 and the male screw 148.

Next, an arrangement of the battery-powered light source connecting unit 150 of the endoscope control section 27 to which the battery-powered light source 101 is attached will be described.

As shown in the figure, the battery-powered light source connecting unit 150 is formed on a side of the endoscope control section 27 to connect and affix the battery type light source 101 to the endoscope control section 27. The battery-powered light source connecting unit 150 is arranged such that the approximately pipe-shaped connecting unit main body 151 is partially inserted into the distal end of a cylindrical light source receiver 152 fixed in the endoscope control section 27 so as to act as a rotation preventing member, and is integrally affixed to the light source receiver 152 by a tightening screw 153.

Formed on the outer surface of the connecting unit main body 151 are a male screw 151a which is screwed into the female screw 112a of the fixing ring 112 and a positioning groove 151b into which the positioning pin 113 disposed on the connecting portion 111 of the battery-powered light source 101 is inserted.

The light source receiver 152 includes a cylindrical space 152a for receiving the lamp unit 140 in the endoscope control section 27. A through-hole 154 serving as an incoming light guide end receiver is formed in the inner surface of the endoscope inserting side of the cylindrical space 152a of the light source receiver 152.

A light guide connector 155 is affixed in the through-hole 154 in a water-tight state. The light guide connector 155 is comprised of a mantle pipe 157 having a cover glass 156 bonded and fixed to the end surface thereof at the cylindrical space 152a side in a water-tight state, and a light guide receiver 158 fixed to the inner surface of the mantle pipe 157. A light guide fiber 34 is inserted through and disposed in the light guide receiver 158. An end of the light guide fiber 34 is integrally affixed to the light guide receiver 158 by a screw 159.

Since the battery-powered light source connecting unit 150 for connecting and fixing the battery-powered light source 101 is arranged as described above and disposed in the endoscope control section 27, there can be obtained a water-tight structure for preventing the invasion of water into the endoscope control section 27 through the battery-powered light source connecting unit 150. The moving distance and the extent of rotation of the switch control section 130 are set such that the word "OFF" printed on the outside surface of the switch control section 130 is located in the vicinity of the index 102 of the light source main body 120 as shown in FIG. 20 in the state shown in FIG. 22, wherein the spring member 115 is abutted against the end of the lamp housing 141 on the distal end of the groove portion thereof. Similarly, the word "ON" of the switch control section 130 is located in the vicinity of the index 102 as shown in FIG. 21 in the state shown in FIG. 23, in which the battery case 146 is abutted against the contact surface of the spring member 115. Other arrangements of the endoscope of the second embodiment are similar to those of the first embodiment.

An operation of the endoscope apparatus 100 arranged as described above will now be discussed.

First, how the battery-powered light source 101 is attached to the control section 27 of the battery-powered light source 101 will be described. The light source lamp 121 and the batteries 131 are placed in their appropriate positions and the battery cap 134 is rotated using a coin or the like to become attached to the control section main body 132 of the switch control section 130 in a water-tight state.

Subsequently, the positioning pin 113 disposed on the connecting portion 111 which constitutes the connecting portion 110 of the battery-powered light source 101 is aligned with the positioning groove 151b of the connecting unit main body 151 in order to connect and affix the battery-powered light source 101 to the battery-powered light source connecting unit 150 of the endoscope control section 27.

In this state, the positioning pin 113 is inserted into the positioning groove 151b and the battery-powered light source 101 is disposed in the battery-powered light source connecting unit 150.

Then, the fixing ring 112 is rotated in a predetermined direction to thereby screw the male screw 151a formed on the outer surface of the connecting unit main body 151 into the female screw 112a of the fixing ring 112. With this operation, the distal end surface of the connecting portion 111 is abutted against the distal end surface of the light source receiver 152 of the endoscope control section 27 so that the battery-powered light source 101 is integrally affixed to and held by the control section 27 as shown in FIG. 20 and FIG. 22.

Figure 22:
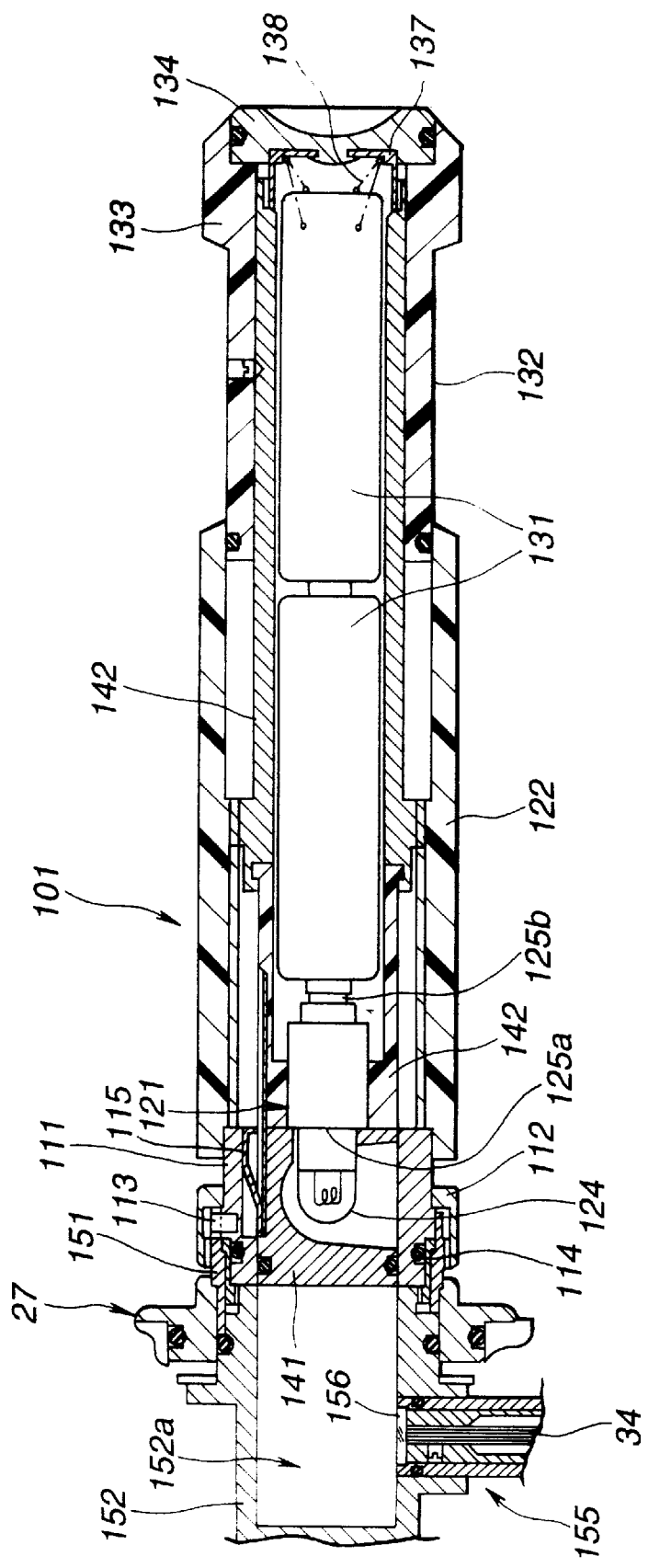

Arranged in this manner, the stepped portion 125a of the base 125 which forms one of the electrodes of the light source lamp 121 in the battery-powered light source 101 is electrically connected to the spring member 115 through the lamp housing 141 and the conduction plate 145 as shown in FIG. 22.

On the other hand, the lamp rear electrode 125b which forms the other electrode of the light source lamp 121 is in direct contact with the positive electrode of one of the batteries 131, while the negative electrode of the other battery 131 is electrically connected to the battery case 146 through the spring 138 and the battery receiver 137.

However, since the spring member 115 is not in electrical contact with the battery case 146, such an arrangement does not provide a circuit through which current can flow to the light source lamp 121. Therefore, the light source lamp 121 is turned off as shown the word "OFF" located in the vicinity of the index 102.

As a result, the word "OFF" marked on the outside surface of the control section main body 132 is located in the vicinity of the index 102 provided with the light source main body 122 of the battery-powered light source 101 as shown in FIG. 20.

The interior of the connecting portion 111 is kept in a water-tight state by the water-tight ring 114 disposed on the connecting portion 111.

Next, the switch control section 130 is rotated by gripping the knob portion 133 of the battery-powered light source 101 in order to execute observation through the endoscope in a state in which the light source lamp 121 is turned on.

Then, the lamp unit 140 in which the battery case 146 and the light source lamp 121 are accommodated gradually moves into the cylindrical space 152a of the endoscope control section 27. In this manner, the control section main body 132 is rotated until the distal end surface thereof is abutted against the base end surface of the small diameter hole portion 122b of the light source main body 122.

Figure 23:
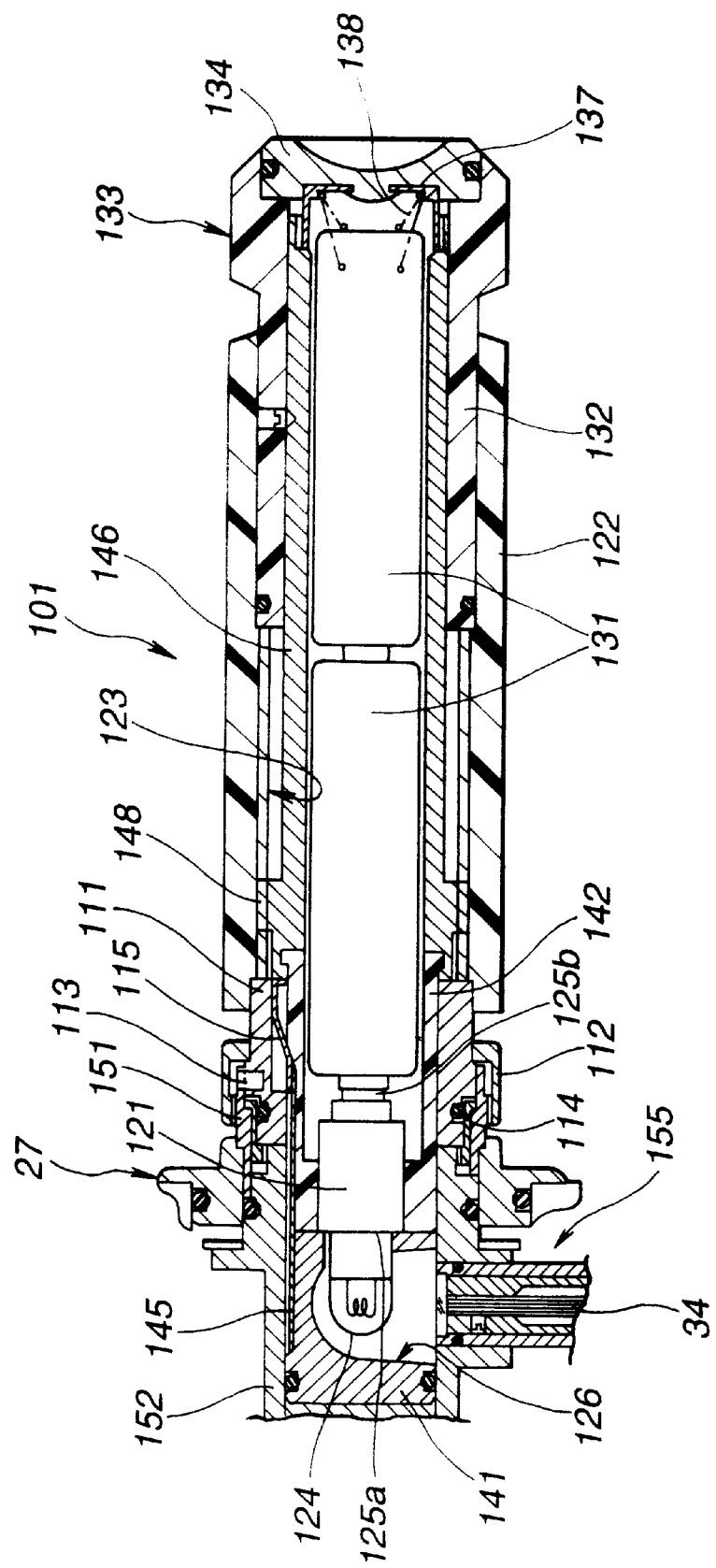

When the distal end surface on the control section main body 132 is abutted against the base end surface of the small diameter hole portion 122b of the light source main body 122 as shown in FIG. 23, the distal end surface of the battery case 146 is abutted against the contact surface of the spring member 115 to thereby form a circuit for supplying current from the dry batteries 131 to the light source lamp 121. With this operation, the light source lamp 121 is turned on.

At the position where the switching operation is finished and the light source lamp 121 is turned on, the lamp housing 141 is disposed in the cylindrical space 152a of the light source receiver 152 so that the reflector surface 126 of the lamp housing 141 confronts the light guide connector 155.

As a result, the light emitted from the light source lamp 121 is reflected by the mirror-finished reflector surface 126 and comes into focus on the incident end surface of the light guide fiber 34 in the light guide connector 155. Then, the illumination light incident on the light guide fiber 34 emerges from the distal end of the inserted portion of the endoscope and illuminates the tissue to be viewed or the like.

The battery case 146 moves in the light source main body 122 while rotating. However, since the lamp receiver 142 is rotatably engaged with the battery case 146 and the spring member 115 which is inserted into the groove portion 144 extending into the lamp housing 141 acts a rotation preventing member, when the lamp housing 141 is disposed in the light source receiver 152 of the endoscope, the reflector surface 126 is always pointed toward the light guide connector 155.

When the light source lamp 121 is turned on as shown in FIG. 21, the display of "ON" marked on the control section main body 132 is located in the vicinity of the index 102 marked on the light source main body 122.

Upon completion of the observation procedure through the endoscope, the switch control section 130 of the battery-powered light source 101 is rotated in a direction opposite to the direction for switching from a turned-off state to a turned-on state to turn off the light source lamp 121.

With this operation, the control section main body 132 retracts to thereby shut off the electrical contact between the spring member 115 and the battery case 146 so that the light source lamp 121 is turned off. The rotation of the control section main body 132 is stopped upon abutment of the spring member 115 against the end portion of the lamp housing 141 on the distal end of the groove. With this operation, the lamp housing 141 is completely accommodated in the connecting portion 111.

After the endoscope is used, the endoscope and the battery-powered light source 101 can be sterilized by being dipped into various types of liquid medicines because they have a water-tight structure which prevents the invasion of water thereinto from the outside regardless of whether they are connected to each other or separated from each other.

As described above, whether the light source lamp of the battery-powered light source is turned on or not can be instantly discerned at a glance from the extended or contracted state of the entire length of the battery-powered light source fixed to the endoscope control section and from the corresponding change of the outside appearance of the battery-powered light source. These features prevent the operator from forgetting to turn off the switch and the batteries from becoming unusable to battery exhaustion when they are used next time.

Since the light source components such as the light source lamp, the reflector surface and the like are completely accommodated in the connecting portion when the light source lamp is not turned on, deposits of dirt and dust on the light source components can be prevented when the battery-powered light source is stored. This can prevent a disadvantage such as a reduction in the amount of emerging light caused by deposits of dirt and dust, abnormal heating due to heat being absorbed by such deposits, and the like.

Further, since the light source lamp portion is accommodated in the endoscope control section when the light source lamp is turned on, the extent that the battery-powered light source projects from the endoscope control section can be reduced to thereby make the outside appearance of the endoscope apparatus compact when it is used.

Since the light source lamp portion which generates the greatest amount of heat is disposed in the endoscope control section, the direct transmission of heat from the light source lamp to the surgeon who holds the endoscope can be prevented. Operability can therefore be improved by this arrangement. Other functions and operations of the second embodiment are the same as those of the first embodiment.

A third embodiment of the present invention will be described with reference to FIG. 24 and FIG. 25.

Figure 24:
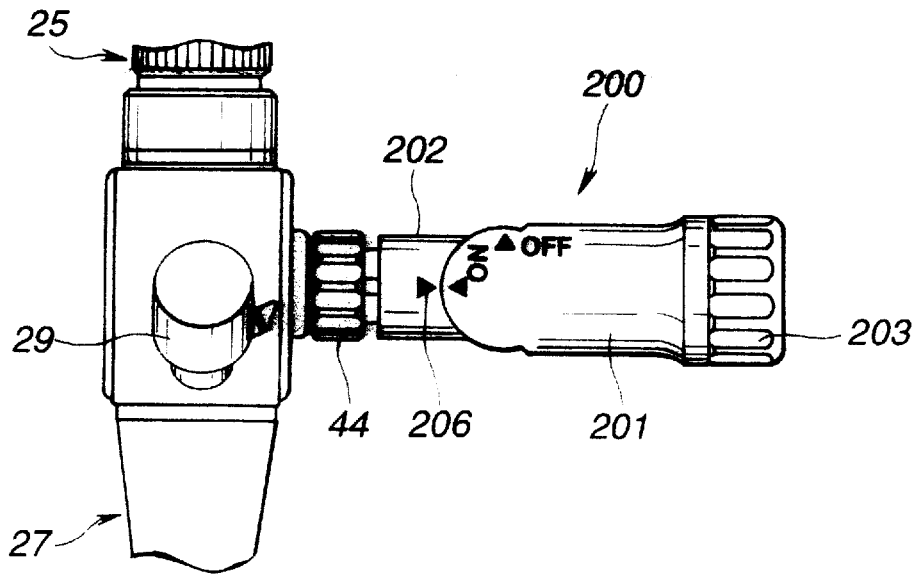
Figure 24:
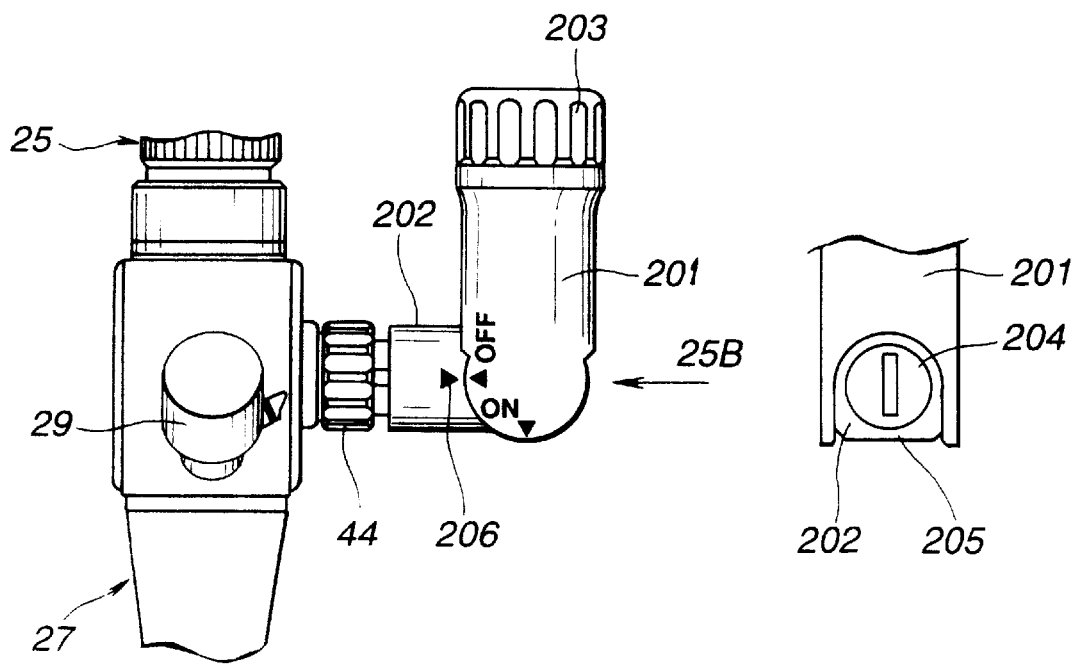

As shown in FIG. 24, the embodiment is arranged such that when a battery accommodating unit 201 of a battery-powered light source 200 is made vertical to an endoscope control section 27, a light source lamp is turned on by being supplied with electrical power. When the battery accommodating unit 201 of the battery-powered light source 200 is rotated by about 90° with respect to a lamp accommodating holder 202 from the above position such that the battery accommodating unit 201 is positioned to be approximately parallel with the endoscope control section 27 as shown in FIG. 25A, the electrical power supplied to the light source lamp is shut off.

A lamp holder mounting/dismounting slit 205 formed in a lamp holder mounting screw portion 204 disposed at the base end portion of the lamp accommodating holder 202 is exposed to the outside. The lamp can be replaced by removing the lamp holder from the lamp accommodating holder 202 by loosening the holder mounting screw portion 204 by a coin or the like inserted into the lamp holder mounting/dismounting slit 205.

That is, when the battery accommodating unit 201 is positioned vertically with respect to the endoscope control section 27 as shown in FIG. 24, the base end portion of the battery accommodating unit 202 in which the light source lamp is disposed is hidden by the battery accommodating unit 201.

As a result, when the light source lamp is replaced, a lamp replacing operation must be carried out when the lamp is turned off so that the lamp holder mounting/dismounting slit 205 formed in the holder mounting screw portion 204 is exposed as shown in FIG. 25A and FIG. 25B.

Reference numeral 203 denotes a lid member covering the battery accommodating unit 201. Further, reference numeral 206 denotes an index marked on the outside surface of the lamp accommodating holder 202 and the words "ON" and "OFF" marked on the battery accommodating unit 201 are disposed in the vicinity of the index 206, respectively by rotating the battery accommodating unit 201.

As described above, whether the lamp of the battery-powered light source is turned on or off can be instantly determined at a glance at the positional relationship of the battery-powered light source to the endoscope control section. This arrangement can prevent a user from forgetting to turn off the switch and the battery from becoming unusable due to battery exhaustion when it is used next time.

Further, when the light source lamp is replaced, the lamp is always replaced in a state in which it is turned off. Accordingly, it can be prevented that the lamp is replaced with a new lamp in a state in which the switch is turned on.

Main parts forming the interior of the battery-powered light source are mainly composed of a copper alloy. Since copper alloy has a low electrical resistance, it can be used as an electrically conductive path. Moreover, since copper alloy has a high thermal conductivity, it can diffuse heat generated in the vicinity of the lamp to its periphery. According to this embodiment, the heat from the lamp can be sufficiently diffused to the entire battery-powered light source as well as to the endoscope through the portion where the battery-powered light source is connected to the endoscope, whereby a local temperature increase can be prevented. In addition, a temperature increase of a portion with which a surgeon comes into direct contact can be prevented by covering the above parts with a resin material having low thermal conductivity.

On the other hand, since the battery-powered light source of the present embodiment can be soaked into a liquid medicine together within an endoscope main body, the exterior member is composed of a resin material or stainless steel which is resistant to detergent solution. Further, since the copper alloy used as the electrically conductive path in the battery-powered light source is not resistant to the liquid medicine or detergent solution, it is sealed in a water-tight state by a member formed from a medicine resistant material.

It is apparent that various embodiments of the present invention can be made based on the present disclosure without departing from the spirit and scope thereof. The present invention is not restricted by the specific embodiments described herein except by the accompanying claims.

What is claimed is:

1. An endoscope apparatus which readily indicates whether a lamp is turned on or off by the outside appearance thereof, comprising:
    an endoscope having a light guide fiber for guiding illumination light and an endoscope control section; and
    a battery-powered light source detachably mounted on the endoscope, the battery-powered light source having a battery accommodating unit for accommodating a battery, the battery accommodating unit being rotatable with respect to the endoscope control section between a first position in which a longitudinal axis of the battery accommodating unit and a longitudinal axis of the endoscope control section are parallel with each other and a second position in which a longitudinal axis of the battery accommodating unit is at an angle with respect to the longitudinal axis of the endoscope control section, in one of the first and second positions, a lamp being turned on and, in the other of the first and second positions, the lamp being turned off.

2. An endoscope apparatus according to claim 1, wherein the battery-powered light source is mounted on and dismounted from the endoscope through a mounting/dismounting portion disposed in the endoscope control section.

3. An endoscope apparatus according to claim 1, wherein the endoscope and the battery-powered light source are arranged to have a water-tight structure when they are detached from each other and also when they are connected to each other.

4. An endoscope apparatus according to claim 1, wherein the battery-powered light source includes
    a lamp for supplying illumination light to the endoscope;
    a lamp accommodation holder for accommodating the lamp; and
    a light source main body unit to which the battery accommodating unit is connected.

5. An endoscope apparatus according to claim 4, wherein an extent of rotation of the light source main body with respect to the lamp accommodation holder is regulated by a rotation regulating ring.

6. An endoscope apparatus according to claim 4, wherein the longitudinal axis of the endoscope control section is the optical axis of an eye contact portion of the control section and, in the first position, a longitudinal axis of the battery accommodating unit is parallel to the optical axis of the eye contact portion of the control section to turn the lamp on, and, in the second position, the longitudinal axis of the battery accommodating unit is at an angle with respect to the optical axis of the eye contact portion of the control section to turn the lamp off.

7. An endoscope apparatus according to claim 4, wherein the longitudinal axis of the endoscope control section is the optical axis of an eye contact portion of the control section and, in the first position, the battery accommodating unit is parallel to the optical axis of the eye contact portion of the control section to turn the lamp on, and, in the second position, the battery accommodating unit is at an angle with respect to the optical axis of the eye contact portion of the control section to turn the lamp off.

8. An endoscope apparatus according to claim 7, including a lamp holder mounting screw portion, the lamp holder mounting screw portion being exposed to thereby permit the lamp to be replaced when the battery accommodating unit is in the position parallel to the endoscope control section.

9. An endoscope apparatus according to claim 1, wherein the battery accommodating unit comprises
    an insulating exterior member;
    an electrically conductive member disposed along an inner surface of the exterior member; and
    a rotation preventing member connected to the electrically conductive member and the exterior member to thereby affix them integrally with each other.

10. An endoscope apparatus which readily indicates whether a lamp is turned on or off by the outside appearance thereof, comprising:
    an endoscope having a light guide fiber for guiding illumination light and an endoscope control section;
    a battery-powered light source detachably mounted on the endoscope such that a lamp is switchable between a turned-on state and a turned-off state by changing a relative position between the battery-powered light source and the endoscope while the battery-powered light source is mounted on the endoscope, the battery-powered light source including the lamp for supplying illumination light to the endoscope, a lamp accommodation holder for accommodating the lamp, a battery for turning on the lamp, and a light source main body unit having a battery accommodating unit for accommodating the battery, wherein the light source main body unit is rotatable with respect to the lamp accommodation holder, an extent of rotation of the light source main body unit with respect to the lamp accommodation holder being regulated by a rotation regulating ring, and wherein the battery accommodating unit includes a contact spring which is abutted against the lamp accommodating holder, and the battery-powered light source further includes an insulating member having a groove in which an electrical contact portion of a lamp unit is disposed, wherein the lamp is turned on or off by abutting an electrode of the battery against the electrical contact portion or the insulating member by rotating the battery accommodating unit with respect to the lamp accommodating holder.

11. An endoscope apparatus which readily indicates whether a lamp is turned on or off by the outside appearance thereof, comprising:

an endoscope having a light guide fiber for guiding illumination light and an endoscope control section;

a lamp for supplying illumination light to the endoscope; and a battery-powered light source detachably mounted on the endoscope such that the lamp is switchable between a turned-on state and a turned-off state by changing a relative position between the battery-powered light source and the endoscope while the battery-powered light source is mounted on the endoscope, wherein said battery-powered light source includes:

the lamp for supplying illumination light to the endoscope;

a battery case for accommodating the battery;

a lamp unit for accommodating the lamp and which is rotatably engaged with the battery case; and a switch control section to which the battery case is fixed integrally therewith, wherein the switch control section advances toward and retracts from a light source main body integrally attached to a light source connecting portion of the endoscope.

12. An endoscope apparatus according to claim 8, wherein the lamp accommodated in the lamp unit is disposed in a cylindrical space of the light source connecting portion by advancing the switch control section toward the light source main body.

13. An endoscope apparatus according to claim 12, wherein the switch control section advances to a predetermined position in the cylindrical space to electrically connect the lamp to the battery to turn the lamp on.

14. An endoscope apparatus according to claim 13, wherein the switch control section retracts to a position such that the lamp is disposed in the light source main body unit when the lamp is turned off, whereby deposit of dirt and dust on the lamp is prevented.

15. An endoscope apparatus according to claim 13, further comprising a circuit for supplying current from the battery to the lamp, the circuit comprising:

a lamp rear electrode which is in direct contact with one of the electrodes of the battery;

a lamp housing abutted against the base of the lamp;

an electrically conductive plate disposed in a groove portion formed in the lamp housing and in a lamp receiver;

a spring member disposed in the connecting portion and which is in contact with the electrically conductive plate;

a battery case which is in contact with the spring member;

a battery receiver screwed into and fixed to the battery case; and a spring which is in direct contact with the other electrode of the battery disposed in the battery receiver.

16. An endoscope apparatus according to claim 15, wherein the lamp housing is disposed in the cylindrical space without rotating therein by inserting the spring member disposed in the connecting portion into the groove portion formed in the lamp housing and in the lamp receiver and in which the electrically conductive plate is disposed.

17. An endoscope apparatus which readily indicates whether a lamp is turned on or off by the outside appearance thereof, comprising:

an endoscope having a light guide fiber for guiding illumination light and an endoscope control section; and a battery-powered light source detachably mounted on the endoscope, the battery-powered light source having a unit which is rotatable with respect to the endoscope control section, said unit being rotatable by a predetermined amount from a first angular state inclusive of zero degrees of an angle formed between a longitudinal axis of said unit which is rotatable and the longitudinal axis of said endoscope control unit to a second angular state thereof different from said first angular state, in one of said first and second angular states, a lamp of said battery-powered light source being turned on and, in the other of said first and second angular states, said lamp being turned off.

18. An endoscope apparatus which readily indicates whether a lamp is turned on or off by the outside appearance thereof, comprising:

an endoscope having a light guide fiber for guiding illumination light and an endoscope control section; and a battery-powered light source detachably mounted on the endoscope, the battery-powered light source having a projected part of a light source main body unit, said projected part being rotatable by a predetermined amount from a first angular state inclusive of zero degrees of an angle formed between a longitudinal axis of said projected part and the longitudinal axis of said endoscope control unit to a second angular state thereof different from said first angular state, in one of said first and second angular states, a lamp of said battery-powered light source being turned on and, in the other of said first and second angular states, said lamp being turned off.

19. An endoscope apparatus which readily indicates whether a lamp is turned on or off by the outside appearance thereof, comprising:

an endoscope having a light guide fiber for guiding illumination light and an endoscope control section; and a battery-powered light source detachably mounted on the endoscope and having a length, the battery-powered light source having:

a lamp for supplying illumination light to said endoscope;

a lamp unit in which the lamp is accommodated; and a switch control unit structured and arranged with respect to the lamp unit so as to be able to advance or retract, to thereby vary between a first state in which the length has been made long and a second state in which the length has been made short, in one of said first and second states, a lamp of said battery-powered light source being turned on and, in the other of said first and second angular states, said lamp being turned off.

* * * * *